US008460896B2

(12) United States Patent
Crowell

(10) Patent No.: US 8,460,896 B2
(45) Date of Patent: Jun. 11, 2013

(54) HOST CELLS AND CULTURE METHODS

(75) Inventor: Christopher K. Crowell, Erie, CO (US)

(73) Assignee: Amgen Inc., Thousand Oaks, CA (US)

(*) Notice: Subject to any disclaimer, the term of this patent is extended or adjusted under 35 U.S.C. 154(b) by 0 days.

(21) Appl. No.: 13/476,959

(22) Filed: May 21, 2012

(65) Prior Publication Data

US 2013/0065271 A1 Mar. 14, 2013

Related U.S. Application Data

(60) Division of application No. 12/785,371, filed on May 21, 2010, now Pat. No. 8,247,210, which is a continuation of application No. 11/634,757, filed on Dec. 6, 2006, now Pat. No. 7,888,101.

(60) Provisional application No. 60/749,076, filed on Dec. 8, 2005.

(51) Int. Cl.
*C12P 21/06* (2006.01)
*C12N 9/00* (2006.01)
*C12N 9/26* (2006.01)
*C12N 1/20* (2006.01)
*C12N 15/00* (2006.01)

(52) U.S. Cl.
USPC ....... 435/69.1; 435/183; 435/201; 435/252.3; 435/320.1; 530/350

(58) Field of Classification Search
None
See application file for complete search history.

(56) References Cited

U.S. PATENT DOCUMENTS

| 4,667,016 A | 5/1987 | Lai et al. |
| 4,703,008 A | 10/1987 | Lin |
| 5,272,071 A | 12/1993 | Chappel |
| 2007/0141674 A1 | 6/2007 | Crowell |

FOREIGN PATENT DOCUMENTS

| WO | WO 91/05867 | 5/1991 |
| WO | WO 91/09955 | 7/1991 |
| WO | WO 95/05465 | 2/1995 |
| WO | WO 00/24782 | 5/2000 |
| WO | WO 00/24893 | 5/2000 |
| WO | WO 00/65070 | 11/2000 |
| WO | WO 01/81405 | 11/2001 |
| WO | WO 02/00856 | 1/2002 |
| WO | WO 2004/081201 | 9/2004 |

OTHER PUBLICATIONS

Chang et al., "N-acetylcysteine Increases the biosynthesis of recombinant EPO in apoptotic Chinese hamster ovary cells," *Free Radical Res.* 30:85-91 (1999).
Chotigeat et al., "Role of environmental conditions on the expression levels, glycoform pattern and levels of sialyltransferase for hFSH produced by recombinant CHO cells," *Cytotechnology* 15:217-221 (1994).
Chung et al., "Effect of sodium butyrate on glycosylation of recombinant erythropoietin," *J. Microbiol. Biotechnol.* 11:1087-1092 (2001).
Cotes et al., "Bio-Assay of erythropoietin in mice made polycythaemic by exposure to air at a reduced pressure," *Nature* 191:1065-1067 (1961).
Davie, "Inhibition of histone deacetylase activity by butyrate," *J. Nutr.* 2845S-2493S (2003).
Della Ragione et al., "Genes modulated by histone acetylation as new effectors of butyrate activity," *FEBS Lett.* 499:199-204 (2001).
Doetschman et al., "Targeted correction of a mutant HPRT gene in mouse embryonic stem cells," *Nature*, 330:576-578 (1987).
Doetschman et al., "Targetted mutation of the *Hprt* gene in mouse embryonic stem cells," *Proc. Natl. Acad. Sci. USA* 85:8583-8587 (1988).
Ellgaard et al., "ER quality control: towards an understanding at the molecular level," *Curr. Opin. Cell Biol.* 13:431-437 (2001).
Ellgaard et al., "Setting the standards: Quality control in the secretory pathway," *Science* 286:1882-1888 (1999).
Gonzalez et al., "Identification, expression, and characterization of a cDNA encoding human endoplasmic reticulum mannosidase I, the enzyme that catalyzes the first mannose trimming step in mammalian Asn-linked oligosaccharide biosynthesis," *J. Biol. Chem.* 274:21375-21386 (1999).
Grinna et al., "Substrate specificities of rat liver microsomal glucosidases which process glycoproteins," *J. Biol. Chem.* 255:2255-2258 (1980).
Hendrick et al., "Increased productivity of recombinant tissular plasminogen activator (t-PA) by butyrate and shift of temperature: a cell cycle phases analysis," *Cytotechnology* 36:71-83 (2001).
Hurtley et al., "Protein oligomerization in the endoplasmic reticulum," *Ann. Rev. Cell Biol.* 5:277-307 (1989).
Iacomino et al., "Transcriptional response of a human colon adenocarcinoma cell line to sodium butyrate," *Biochem. Biophys. Res. Comm.* 285:1280-1289 (2001).
Jakob et al., "Degradation of misfolded endoplamic reticulum glycoproteins in *Saccharomyces cerevisiae* is determined by a specific oligosaccharide structure," *J. Cell Biol.* 142:1223-1233 (1998).
Joseph et al., "Expression profiling of sodium butyrate (NaB)-treated cells: identification of regulation of genes related to cytokine signaling and cancer metastasis by NaB," *Oncogene* 23:6304-6315 (2004).
Kim et al., "Overexpression of bcl-2 inhibits sodium butyrate-induced apoptosis in Chinese hamster ovary cells resulting in enhanced humanized antibody production," *Biotech. Bioeng.* 71:184 (2001).
Kornfeld et al., "Assembly of asparagine-linked oligosaccharides," *Ann. Rev. Biochem.* 54:631-664 (1985).
Kucherlapati et al., "Homologous recombination in mammalian somatic cells," *Prog. Nucl. Acid Res. & Mol. Biol.* 36:301-310 (1989).
Liu et al., "Oligosaccharide modification in the early secretory pathway directs the selection of a misfolded glycoprotein for degradation by the proteasome," *J. Biol. Chem.* 274:5861-5867 (1999).

(Continued)

*Primary Examiner* — Christian Fronda
(74) *Attorney, Agent, or Firm* — Michael G. Penn

(57) ABSTRACT

Improved host cells and culture methods involving overexpression of MAN1C1 activity to improve protein production are provided.

17 Claims, 4 Drawing Sheets

OTHER PUBLICATIONS

Mariadason et al., "Genetic reprogramming in pathways of colonic cells maturation by short chain fatty acids: Comparison with trichostatin A, sulindac, and curcumin and implications for chemoprevention of colon cancer," *Cancer Res.* 60:4561-4572 (2000).

Molinari et al., "Role of EDEM in the release of misfolded glycoproteins from the calnexin cycle," *Science* 299:1397-1400 (2003).

NCBI Genbank Accession No. AB209275.

NCBI Genbank Accession No. AF261655.

NCBI Genbank Accession No. DV567987.

Oda et al., "EDEM as an acceptor of terminally misfolded glycoproteins released from calnexin," *Science* 299:1394-1397 (2003).

Prasad et al., "Effect of sodium butyrate on mammalian cells in culture: A review," *In Vitro* 12:125-132 (1976).

Sauer et al., "Manipulation of transgenes by site-specific recombination: Use of cre recombinase," *Meth. Enzymol.* 225:890-900 (1993).

Sauer, "Site-specific recombination: developments and applications," *Curr. Opin. Biotechnol.* 5:521-527 (1994).

Sifers, "Protein degradation unlocked," *Science* 299:1330-1331 (2003).

Sung et al., "Effect of sodium butyrate on the production, heterogeneity and biological activity of human thrombopoietin by recombinant Chinese hamster ovary cells," *J. Biotechnol.* 112:323-335 (2004).

Tabuchi et al., "Identification of genes responsive to sodium butyrate in colonic epithelial cells," *Biochem. Biophys. Res. Comm.* 293:1287-1294 (2002).

Thomas et al., "High frequency targeting of genes to specific sites in the mammalian genome," *Cell* 44:419-428 (1986).

Thomas et al, "Site-directed mutagenesis by gene targeting in mouse embryo-derived stem cells," *Cell* 51:503-512 (1987).

Tremblay et al., "Molecular cloning, chromosomal mapping and tissue-specific expression of a novel human α1,2-mannosidase gene involved N-glycan maturation," *Glycobiology* 8:585-595 (1998).

Tremblay et al., "Characterization of a cDNA encoding a novel human golgi α1,2-mannosidase (IC) involved in N-glycan biosynthesis," *J. Biol. Chem.* 275:31655-31660 (2000).

Yuan et al., "Effect of butyrate on the expression of microinjected or transfected genes," *J. Biol. Chem.* 260:3778-3783 (1985).

International Search Report, International Application No. PCT/US2006/046443, mailed Oct. 17, 2007.

Crowell, "Sodium butyrate impacts the expression of genes associated with erythropoietin glycosylation," *Abstracts of Papers American Chemical Society* 229:U212 (Abstract #218), 2005.

Werner et al., "Appropriate mammalian expression systems for biopharmaceuticals," *Drug Res.* 48: 870-880, 1998.

Yoon et al., "Effect of simultaneous application of stressful culture conditions on specific productivity and heterogeneity of erythropoietin in Chinese hamster ovary cells," *Biotechnol. Prog.* 20: 1293-1296, 2004.

Chica et al., Curr. Opin. Biotechnol. Aug. 2005; 16(4):378-84.

Sen et al., Appl Biochem Biotechnol. Dec. 2007; 143(3):212-23.

Hosokawa et al., J Biol Chem. Jul. 11, 2003; 278(28):26287-94. Epub May 6, 2003.

European Office Communication dated Mar. 12, 2010 for EP Appl. No. 06844853.9.

rHuEPO Specific Productivity (Day 1-5)

MAN1C mRNA Levels rHuEPO mRNA Levels

HOST CELLS AND CULTURE METHODS

The present application is a divisional of U.S. patent application Ser. No. 12/785,371, filed May 21, 2010, now U.S. Pat. No. 8,247,210, which is a continuation of U.S. patent application Ser. No. 11/634,757, filed Dec. 6, 2006, now issued as U.S. Pat. No. 7,888,101, which claims benefit under 35 U.S.C. §119 of U.S. Patent Application No. 60/749,076, which was filed Dec. 8, 2005, each of which are hereby incorporated herein by reference in their entirety.

The present application is being filed along with a Sequence Listing in text format. The Sequence Listing is provided as a file entitled A-1072-US-DIV_RevisedSeqListing.TXT created Oct. 16, 2012, which is 27 KB in size. The information in the text format of the Sequence Listing is incorporated herein by reference in its entirety.

FIELD OF THE INVENTION

The invention relates to improved host cells and culture methods that improve glycoprotein production.

BACKGROUND OF THE INVENTION

Methods of increasing recombinant host protein production in the pharmaceutical industry and in the laboratory are highly desirable in many ways, including cost savings, times savings, and manufacturing capacity. Treatment with sodium butyrate has been one means of increasing protein production in cell culture in commercial biopharmaceutical processes. However, the derived benefit of increased protein yields is sometimes offset by the toxic side effects of sodium butyrate.

Sodium butyrate is a short chain fatty acid that inhibits the histone deacetylase (HDAC) enzyme responsible for the maintenance of chromatin structure in the nucleus of cells (Davie, *J. Nutrition* 133: 2485S-2493S, 2003). The loss of activity results in an alteration in transcriptional regulation of genes through the normal acetylation and deacetylation process of histones (Prasad et al., In Vitro 12: 125-132, 1976). The change in transcriptional regulation has been shown to increase the specific productivity of cell lines producing recombinant proteins in vitro. For example, sodium butyrate has been shown to increase the synthesis of secreted recombinant follicle stimulating hormone (FSH), tissue plasminogen activator (tPA), erythropoietin (EPO), and thrombopoietin (TPO) in Chinese hamster ovary (CHO) cells (Sung et al., *J. Biotechnology* 112: 323-335, 2004; Hendrick et al. *Cytotechnology* 36: 71-83, 2001; Chung et al., *J. Microbiol. Biotechnol.* 11, 1087-1092, 2001; Chotigeat et al., *Cytotechnology* 15: 217-221, 1994; Chang et al., *Free Radical Research* 30: 85-91, 1999). The precise mechanisms responsible for these increases are uncertain. Sodium butyrate treatment has been shown to transiently increase mRNA levels for recombinant protein, resulting in increases in resulting protein biosynthesis (Yuan et al., *J. Biol. Chem.* 260: 3778-3783, 1985).

Changes in gene expression caused by sodium butyrate have been studied previously in cell lines involved in colon cancer research. The studies demonstrated that sodium butyrate alters the expression of multiple genes involved in cell cycle progression, differentiation, cytokine signaling, and apoptosis. However, such studies were limited to relatively a small subset of genes and did not determine whether genes were involved in protein biosynthesis. (Joseph et al., *Oncogene* 23: 6304-6315, 2004; Tabuchi et al., *Biochem. Biophys. Research Comm.* 293: 1287-1294, 2002; Iacomino et al., *Biochem. Biophys. Research Comm.* 285: 1280-1289, 2001; Mariadason et al., *Cancer Res.* 60: 4561-4572, 2000; Della Ragione et al., *FEBS Letters* 499, 199-204, 2001).

Alpha 1,2 mannosidase I enzyme (MAN1C1) is an enzyme involved in glycoprotein N-linked oligosaccharide processing that has been described in Tremblay et al. (*Glycobiology* 8: 585-595, 1998) and Gonzalez et al. (*J. Biol. Chem.* 274: 21375-21386, 1999). The enzyme catalyzes the first mannose trimming step associated with processing of high mannose oligosaccharide structures by removing a terminal mannose sugar from the oligosaccharide. N-terminal glycosylation involves the addition and removal of various monosaccharide sugars in both the endoplasmic reticulum (ER) and Golgi compartments (Kornfeld et al., *Ann. Rev. Biochem.* 54: 631-664, 1985). In the ER, the N-linked glycosylation is accompanied by the folding of nascent glycoproteins into their native structure through interactions with molecular chaperones (Ellgaard et al., *Science* 286: 1882-1888, 1999; Jakob et al., *J. Cell Biol.* 142: 1223-1233, 1998). This process has been termed ER quality control, and if the process is blocked due to a misfolded protein, the onset of ER associated degradation, or ERAD, of the protein typically occurs (Ellgaard et al., *Curr. Opin. Cell Biol.* 13: 431-437, 2001; Sifers, *Science* 299: 1330-1331, 2003; Oda et al., *Science* 299: 1394-1397, 2003; Molinari et al., *Science* 299:1397-1400, 2003; Hurtley et al., *Ann. Rev. Cell Biol.* 5: 277-307, 1989). The removal of a terminal mannose sugar from $Man_9$ to $Man_8$ by the alpha 1,2 mannosidase I enzyme (MAN1C1) has been shown to affect the onset of the ERAD response (Liu et al., *J. Biol. Chem.* 274: 5861-5867, 1999; Grinna et al. *J. Biol. Chem.* 255, 2255-2258, 1980).

In view of the toxicity of protein production inducers such as sodium butyrate, there exists a need for other means of increasing overall production of recombinant proteins in cell culture.

SUMMARY OF THE INVENTION

The present invention provides host cells engineered to overexpress alpha 1,2 mannosidase (MAN1C1) and a glycoprotein or protein of interest. Such host cells may comprise a heterologous expression control sequence operably linked to a nucleic acid encoding MAN1C1, and a heterologous expression control sequence operably linked to a nucleic acid encoding such glycoprotein. The host cells may engineered to overexpress either or both MAN1C1 and the glycoprotein of interest by any means known in the art, including transfection with a vector comprising a nucleic acid encoding the protein, wherein the nucleic acid is operably linked to a heterologous expression control sequence, or transfection with an expression control sequence that upregulates expression of endogenous protein.

The invention further provides methods of producing a glycoprotein of interest comprising the steps of: culturing any of the host cells of the invention in culture medium; and recovering such glycoprotein from the host cell or culture medium. Such a host cell is cultured under conditions that induce increased MAN1C1 protein expression or increased specific productivity of the glycoprotein of interest. It is further contemplated that such a host cell expresses MAN1C1 protein at a level that increases the amount (pg/mg protein) or specific productivity (pg/cell/day) of such glycoprotein produced. Improvements in such glycoprotein production or specific productivity may be, e.g., at least 2-fold, 3-, 4-, 5-, 6-, 7-, 8-, 9-, 10-, 15-, or 20-fold or higher.

The invention also contemplates methods of increasing production of a glycoprotein of interest comprising the step of further adding an inducer of protein production to the culture medium. Inducers of protein production are well known to one of skill in the art and are further provided herein.

The host cells and methods of the invention may be used to produce any glycoprotein or protein of interest. Exemplary glycoproteins include erythropoiesis-stimulating molecules such as erythropoietin or darbepoetin, or analogs, variants, or derivatives thereof. Host cells of the invention may be, but are not limited to, mammalian cells, CHO cells, human cells, BHK cells, NS/0 cells, HT-1080 cells, or any other cell known to be useful in one of skill in the art.

In another aspect, the invention provides methods of screening for an inducer of protein production comprising the steps of: contacting a host cell with a candidate compound, determining expression level of MAN1C1, and identifying said candidate compound as an inducer of protein production if the expression level of MAN1C1 increases. Such a method contemplates determining mRNA expression levels or protein expression levels.

Other features and advantages of the invention will become apparent from the following detailed description. It should be understood, however, that the detailed description and the specific examples, while indicating exemplary embodiments of the invention, are given by way of illustration only, because various changes and modifications within the spirit and scope of the invention will become apparent to those skilled in the art from this detailed description.

DETAILED DESCRIPTION OF THE INVENTION

Figure 1:
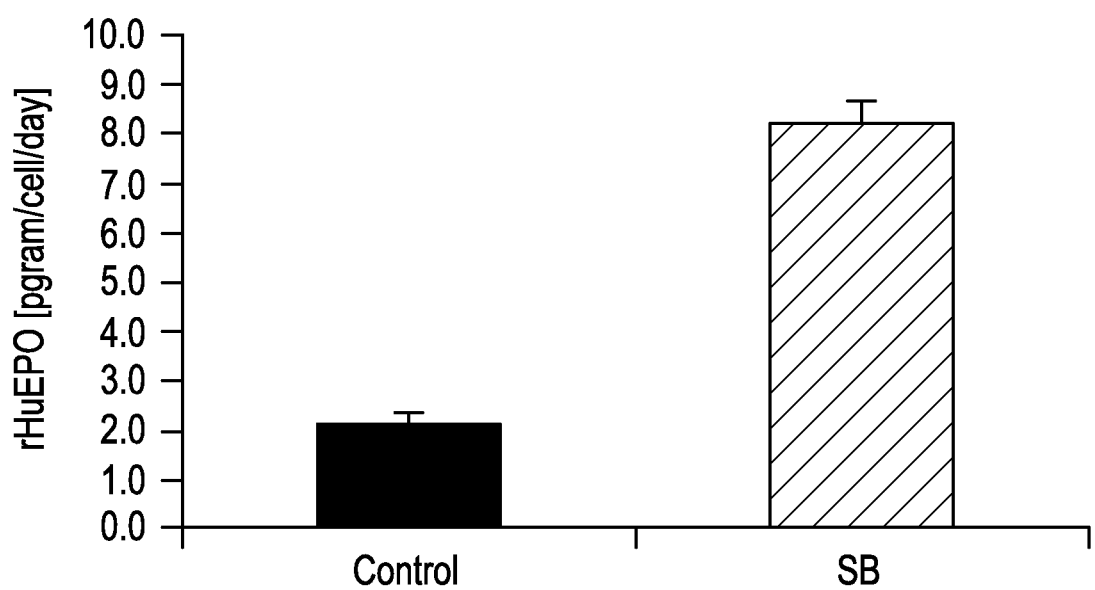
FIG. 1 displays measured rHuEPO specific productivity ($Q_P$) over 5-day culture in the presence of sodium butyrate (SB) and absence (control) of 2 mM sodium butyrate.

The present invention provides materials and methods for increasing the recombinant production of a protein of interest in host cells. As used herein, a "protein of interest" is a protein (other than MAN1C1) for which the recombinant production of bulk quantities of such protein is desired.

More specifically, the invention includes host cells producing a recombinant protein of interest that have been additionally engineered to overexpress alpha 1,2 mannosidase I enzyme (MAN1C1), cell cultures containing such host cells, and methods of producing increased amounts of the recombinant protein of interest comprising culturing such host cells under conditions such that MAN1C1 is expressed at levels higher than normal. The expression of higher levels of MAN1C1 results in improvements in specific productivity and/or protein production of the protein of interest.

The invention also contemplates methods of improving protein production or increasing specific productivity involving increasing the levels of MAN1C1 activity in host cells through introduction of chemical inducers that increase MAN1C1 protein production, or chemical inducers that increase the specific activity of MAN1C1 expressed.

The invention contemplates methods wherein the improved specific productivity measures at least 2 pg glycoprotein/cell/day. In exemplary embodiments, the specific productivity measures at least 3, 4, 5, 6, 7, 8, 9, 10, 11, 12, 13, 14, 15, 20, 25, 30, 35, 40, 45, 50, 60, 70, 80, 90, or 100 pg glycoprotein/cell/day. However, greater specific productivity is contemplated, especially with the use of additional inducers.

The present invention determined that one mechanism by which sodium butyrate increases protein production is through upregulating expression of MAN1C1, a gene involved in glycosylation of proteins. The data described herein show that high levels of MAN1C1 expression do not significantly alter glycosylation of glycoproteins but unexpectedly increase the amount of recombinant protein produced. MAN1C1 mRNA expression was shown to dramatically increase when cells were treated with sodium butyrate, to roughly 10-fold higher over a 24 hour period and greater than 40-fold over five day period. Treatment of host cells expressing a recombinant protein of interest with siRNA to reduce MAN1C1 protein expression reduced by 50% the sodium butyrate-induced increase in production of the protein of interest. Moreover, overexpression of MAN1C1 in the absence of sodium butyrate resulted in a 2-3 fold increase in production of the protein of interest. Thus, the increased expression of MAN1C1 contributes to the increase in specific productivity of the protein of interest.

The term "isolated nucleic acid" refers to a nucleic acid of the invention that is free from at least one contaminating nucleic acid with which it is naturally associated. A "nucleic acid" refers to a DNA or RNA sequence, optionally including artificial bases or base analogs.

The term "identity" (or "percent identical") is a measure of the percent of identical matches between the smaller of two or more sequences with gap alignments (if any) addressed by a particular mathematical model or computer program (i.e., "algorithms"). The term "similarity" is a related concept but, in contrast to "identity", includes both identical matches and conservative substitution matches. Identity and similarity of related nucleic acid molecules and polypeptides can be readily calculated by known methods. Preferred methods to determine identity and/or similarity are designed to give the largest match between the sequences tested. Methods to determine identity and similarity are described in publicly available computer programs. Exemplary computer program methods to determine identity and similarity between two sequences include, but are not limited to, the GCG program package, including GAP (Devereux et al., *Nucl. Acids. Res.* 12: 387, 1984; Genetics Computer Group, University of Wisconsin, Madison, Wis.), BLASTP, BLASTN, and FASTA (Altschul et al., *J. Mol. Biol.* 215:403-410, 1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith-Waterman algorithm may also be used to determine identity. Preferred parameters for a polypeptide sequence comparison include the following: Algorithm: Needleman et al., *J. Mol. Biol.* 48: 443-453, 1970; Comparison matrix: BLOSUM 62 from Henikoff et al., *Proc. Natl. Acad. Sci. USA* 89: 10915-10919, 1992); Gap Penalty: 12, Gap Length Penalty: 4; Threshold of Similarity: 0. The GAP program is useful with the above parameters (along with no penalty for end gaps). Preferred parameters for nucleic acid molecule sequence comparisons include the following: Algorithm: Needleman et al., J. Mol. Biol., 48: 443-453, 1970; Comparison matrix: matches=+10, mismatch=0, Gap Penalty: 50, Gap Length Penalty: 3. The GAP program is also useful with the above parameters. Other exemplary algorithms, gap opening penalties, gap extension penalties, comparison matrices, thresholds of similarity, etc. may be used by those of skill in the art.

The term "operably linked" refers to a functional linkage between an expression control sequence and a second nucleic acid sequence, wherein the expression control sequence directs transcription of the nucleic acid corresponding to the second sequence.

The phrase "stringent hybridization conditions" refers to conditions under which a probe will hybridize to its target subsequence, typically in a complex mixture of nucleic acid, but to no other sequences. Hybridization stringency is principally determined by temperature, ionic strength, and the concentration of denaturing agents such as formamide. Examples of "highly stringent conditions" for hybridization and washing are 0.015M sodium chloride, 0.0015M sodium citrate at 65-68° C. or 0.015M sodium chloride, 0.0015M sodium citrate, and 50% formamide at 42° C. See Sambrook, Fritsch & Maniatis, Molecular Cloning: A Laboratory Manual, 2nd Ed., Cold Spring Harbor Laboratory, (Cold Spring Harbor, N.Y. 1989); (1989) and Anderson et al., Nucleic Acid Hybridisation:Hybridization: a practical approach, Ch. 4, IRL Press Limited (Oxford, England). Limited, Oxford, England (1999). Examples of typical "moderately stringent" conditions are 0.015M sodium chloride, 0.0015M sodium citrate at 50-65° C. or 0.015M sodium chloride, 0.0015M sodium citrate, and 20% formamide at 37-50° C. By way of example, a "moderately stringent" condition of 50° C. in 0.015 M sodium ion will allow about a 21% mismatch.

It will be appreciated by those skilled in the art that there is no absolute distinction between "highly" and "moderately" stringent conditions. For example, at 0.015M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

The term "vector" is used to refer to any molecule (e.g., nucleic acid, plasmid, or virus) used to transfer coding information to a host cell.

The term "expression vector" refers to a vector which is suitable for use in a host cell and contains nucleic acid sequences which direct and/or control the expression of desired nucleic acid sequences ("expression control sequences"). Suitable expression control sequences include constitutive or inducible or regulatable promoters, enhancers or an array of transcription factor binding sites. "Expression" includes, but is not limited to, processes leading to protein production such as transcription, translation, and RNA splicing, if introns are present.

A "heterologous" expression control sequence operably linked to a nucleic acid refers to an expression control sequence that is operably linked to a nucleic acid (including a gene) that is different from the gene to which the expression control sequence is normally operably linked in its native state.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

As used herein, a host cell "engineered to overexpress" a protein (or a nucleic acid encoding such protein) is a host cell, including a descendant thereof, that has been altered in such a way that higher levels of such protein are expressed than normal, compared to the unaltered host cell. Thus, included within this category are expression of proteins foreign to the host cell, proteins not naturally expressed by the host cell, or proteins naturally expressed by the host cell at relatively low levels that increase after alteration of the host cell.

The section headings are used herein for organizational purposes only, and are not to be construed as in any way limiting the subject matter described.

Increasing Alpha 1,2-Mannosidase (MAN1C1) Activity

The invention contemplates that increasing the levels of alpha 1,2-mannosidase (MAN1C1) activity in host cells during production of a protein of interest may be accomplished through any means known in the art, including by adding a chemical inducer or through overexpression of MAN1C1 enzyme. The MAN1C1 enzyme that the host cell overexpresses may have the same or similar sequence as a MAN1C1 that is endogenous, or native, to the host cell. Thus, human MAN1C1 may be overexpressed in human host cells, CHO MAN1C1 may be overexpressed in CHO host cells, and similarly native enzyme that carries out the MAN1C1 function may be overexpressed in other host cells. However, any MAN1C1 enzyme that functions in the same way in the desired host cell may be used, including an ortholog, or a biologically active fragment, variant, analog or derivative.

As used herein, "analog" refers to a nucleotide or amino acid sequence that has insertions, deletions or substitutions relative to the parent sequence, while still substantially maintaining the biological activity of the parent sequence, as determined using biological assays known to one of skill in the art. "Variants" include naturally occurring allelic variants, splice variants, or polymorphic forms of the parent sequence. "Derivatives" of naturally occurring, variant or analog polypeptides include those which have been chemically modified, for example, to attach water soluble polymers (e.g., polyethylene glycol), radionuclides, or other diagnostic or targeting or therapeutic moieties, any of which can be attached directly or indirectly through linkers.

"Biologically active" with respect to a MAN1C1 polypeptide means that the fragment, variant, derivative or analog thereof retains similar activity in improving specific productivity, e.g. as measured as amount of protein of interest produced per cell per day, or retains similar enzymatic activity in removing mannose from a suitable mannose-containing substrate. "Biologically active" with respect to a MAN1C1 nucleic acid means that the nucleic acid encodes such a biologically active MAN1C1 polypeptide.

The nucleotide and amino acid sequences of an exemplary human MAN1C1 are set forth in SEQ ID NOS: 1 and 2, respectively. Nucleotides 331 through 2223 of the polynucleotide of SEQ ID NO: 1 encode the MAN1C1 polypeptide of SEQ ID NO: 2. The nucleotide and polypeptide sequences for human MAN1C1 (SEQ ID NOS: 1 and 2, respectively, were identified by Tremblay et al. (J. Biol. Chem. 275: 31655-31660, 2000) and are provided in Genbank Accession No. AF261655. Exemplary polynucleotide and polypeptide sequences of other orthologs and variants of MAN1C1 are identified in Genbank Accession Nos. AB209275 (SEQ ID NOS: 12 and 13) and DV567987 (SEQ ID NO: 14).

The term "MAN1C1" as used herein refers to human MAN1C1 (the polypeptide of SEQ ID NO: 2 encoded by the polynucleotide of SEQ. ID NO: 1), orthologs thereof, or a biologically active fragment, variant, analog, or derivative of the human enzyme or orthologs. Exemplary analogs retain 65% or higher amino acid identity to the parent sequence, or 70%, 75%, 80%, 85%; 90%, 91%, 92%, 93%, 94%, 95%, 96%, 97%, 98%, or 99% or higher identity. Exemplary fragments include fragments of at least 25, 50, 75, 100, or more amino acid residues of a MAN1C1 polypeptide. Other exemplary MAN1C1 fragments, variants, analogs or derivatives include those encoded by nucleic acids that would hybridize under highly or moderately stringent conditions to the nucleotide sequence of SEQ ID NO: 1 or any other orthologs of the nucleotide sequence of SEQ ID NO: 1.

As used herein, the term "MAN1C1 nucleic acid" or "MAN1C1 polynucleotide" refers to a nucleic acid that encodes any of the preceding polypeptides, including a nucleotide sequence as set forth in SEQ ID NO: 1, or nucleic acids comprising nucleotide sequences that are at least about 65%, 70%, 75%, 80%, 85%, 90%, 95%, 96%, 97%, 98%, 99% or 100% identical thereto, or nucleic acids which hybridize under moderately or highly stringent conditions as defined herein with the complement of SEQ ID NO: 1 or any other orthologs of the nucleotide sequence of SEQ ID NO: 1.

It is also understood that MAN1C1 nucleic acids include allelic or splice variants of a MAN1C1 nucleic acid of SEQ ID NO: 1 or any other orthologs, and include nucleotide sequences which are complementary to any of the above nucleotide sequences.

Where a gene encoding a MAN1C1 polypeptide has been identified from one species, all or a portion of that gene may be used as a probe or primer to identify corresponding genes from other species (orthologs, or "species homologs") or related genes from the same species (homologs). The probes or primers may be used for hybridization screening or PCR amplification of genomic DNA or cDNA libraries from various tissue sources believed to express the MAN1C1 gene. Appropriate conditions of hybridization stringency can be determined by one of ordinary skill in the art. Bioinformatic techniques can also be used to identify orthologs, wherein collections of sequences from various mammalian or other species are screened for nucleotide or polypeptide sequences that exhibit significant homology to known MAN1C1 sequences. Nucleic acids encoding MAN1C1 polypeptides may also be identified by expression cloning which employs the detection of positive clones based upon a property of the expressed protein. Typically, nucleic acid libraries are screened by the binding of an antibody or other binding partner (e.g., receptor or ligand) to cloned proteins which are expressed and displayed on a host cell surface. The antibody or binding partner is modified with a detectable label to identify those cells expressing the desired clone.

Although the invention primarily contemplates that MAN1C1 will be overexpressed, i.e., expressed in the altered host cell at a greater level than normal in the unaltered host cell, the invention also contemplates methods for decreasing or inhibiting the expression of MAN1C1 in cells, e.g. through administration of siRNA or antisense compounds.

Inducers of Protein Production

The invention also contemplates the use of other known inducers of protein production in combination with the host cells which overexpress MAN1C1 and another protein of interest, to further increase overall production of the protein of interest. Known inducers include, but are not limited to, the following compounds: N-Acetyl-L-cysteine, Actinomycin D, 7-Amino-, Bafilamycin A1, *Streptomyces griseus*, Calphostin C, *Cladosporium cladosporioides*, Camptothecin, *Camptotheca acuminata*, CAPE, 2-Chloro-2'-deoxyadenosine, 2-Chloro-2'-deoxyadenosine 5'-Triphosphate, Tetralithium Salt, Cycloheximide, Cyclophosphamide Monohydrate, Cyclosporine, *Trichoderma polysporum*, Daunorubicin, Hydrochloride, Dexamethasone, Doxorubicin, Hydrochloride, (−)-Epigallocatechin Gallate, Etoposide, Etoposide Phosphate, ET-18-OCH3, 5-Fluorouracil, H-7, Dihydrochloride, Genistein, 4-Hydroxynonenal, 4-Hydroxyphenylretinamide, Hydroxyurea, IL-1β Inhibitor, (±)-S-Nitroso-N-acetylpenicillamine, S-Nitrosoglutathione, Phorbol-12-myristate-13-acetate, Puromycin, Dihydrochloride, 1-Pyrrolidinecarbodithioic Acid, Ammonium Salt, Quercetin, Dihydrate, Rapamycin, Sodium Butyrate, Sodium 4-Phenylbutyrate, D-erythro-Sphingosine, N-Acetyl-, D-erythro-Sphingosine, N-Octanoyl-, Staurosporine, *Streptomyces* sp., Sulindac, Thapsigargin, TRAIL, *E. coli*, Trichostatin A, *Streptomyces* sp., (±)-Verapamil, Hydrochloride, Veratridine, Vitamin D3, 1α, 25-Dihydroxy-, and Vitamin E Succinate (VWR and Calbiochem).

The invention further contemplates the identification of other chemicals that improve protein production through increasing MAN1C1 activity, for example via increasing MAN1C1 expression. Increases in MAN1C1 activity can be determined as described by Tremblay et al. (2000, supra).

Increases in MAN1C1 expression can be determined by measuring relative amounts of MAN1C1 mRNA produced as described in Example 4 (using Affymetrix chip) or Example 5 (quantitative PCR), or MAN1C1 protein produced via ELISA, HPLC, or other methods known in the art or as described by Tremblay et al. (2000, supra).

Proteins of Interest for Recombinant Production

The recombinant protein of interest that the host cell overexpresses can be any polypeptide, either endogenous (native) or exogenous to the cell. Exemplary proteins of interest are glycoproteins, including secreted glycoproteins. In exemplary embodiments, the glycoprotein of interest is an erythropoiesis-stimulating molecule, described below.

The amount of recombinant protein of interest produced may be measured as "specific productivity," which is the amount of protein of interest produced per cell per day. The amount of recombinant protein of interest produced may also be measured by amount of protein of interest produced per amount of cell protein. Methods of measuring specific productivity or protein production are well known in the art.

The recombinant proteins of interest for which expression can be increased using the materials and methods of the invention can be any polypeptide, either endogenous or exogenous to the cell. Exemplary recombinant proteins of interest are glycoproteins, especially N-glycosylated glycoproteins. Exemplary glycoproteins of interest include secreted glycoproteins such as erythropoiesis-stimulating molecules.

The terms "polypeptide" and "protein" are used interchangeably herein.

The term "erythropoiesis-stimulating molecules" as used herein includes human erythropoietin (SEQ. ID NO.: 3) or a biologically active variant, derivative, or analog thereof, including a chemically modified derivative of such protein or analog. Amino acids 1 through 165 of SEQ ID NO: 3 constitute the mature protein. Another exemplary erythropoiesis-stimulating molecule is darbepoetin (SEQ ID NO: 5). Amino acids 1 through 165 of SEQ. ID NO: 5 constitute the mature protein. Also contemplated are analogs of erythropoietin (SEQ ID NO.: 3) or darbepoetin (SEQ. ID NO: 5), with 65%, 70%, 75%, 80%, 85%, 90%, 91%, 92%, 93%, 94%, 95%, 96%, 97%, 98%, or 99% identity to SEQ. ID NO: 3 or SEQ. ID NO: 5, respectively, and still retaining erythropoietic activity.

Exemplary sequences, manufacture, purification and use of recombinant human erythropoietin are described in a number of patent publications, including but not limited to Lin U.S. Pat. No. 4,703,008 and Lai et al. U.S. Pat. No. 4,667,016, each of which is incorporated herein by reference in its entirety. Darbepoetin is a hyperglycosylated erythropoietin analog having five changes in the amino acid sequence of rHuEPO which provide for two additional carbohydrate chains. More specifically, darbepoetin contains two additional N-linked carbohydrate chains at amino acid residues 30 and 88 of SEQ ID NO: 5. Exemplary sequences, manufacture, purification and use of darbepoetin and other erythropoietin analogs are described in a number of patent publications, including Strickland et al., 91/05867, Elliott et al., WO 95/05465, Egrie et al., WO 00/24893, and Egrie et al. WO 01/81405, each of which is incorporated herein by reference in its entirety. Derivatives of naturally occurring or analog polypeptides include those which have been chemically modified, for example, to attach water soluble polymers (e.g., pegylated), radionuclides, or other diagnostic or targeting or therapeutic moieties.

The term "erythropoietic activity" means activity to stimulate erythropoiesis as demonstrated in an in vivo assay, for example, the exhypoxic polycythermic mouse assay. See, e.g., Cotes and Bangham, *Nature* 191:1065 (1961).

Other polypeptides of interest for which recombinant production can be increased using the materials and methods of the invention include cytokines, immunoglobulin-like proteins, antibodies, and peptibodies, and analogs, variants, or derivatives of any of these proteins.

Exemplary proteins of interest include granulocyte-colony stimulating factor (GCSF), stem cell factor, leptin, hormones, cytokines, hematopoietic factors, growth factors, antiobesity factors, trophic factors, anti-inflammatory factors, receptors or soluble receptors, such as a soluble fragment of p80 TNF-R, enzymes, and Fc-fusions of any of the preceding. Other examples include insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), interleukins (IL-1 to IL-12), tumor necrosis factor (TNF), tumor necrosis factor-binding protein (TNF-bp) or TNF receptor-I or -II, brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase, or kallikrein, receptors or soluble receptors, enzymes, variants, derivatives, or analogs including Fc-fusions of any of these proteins.

As used herein, the term "antibody" includes fully assembled antibodies, monoclonal antibodies (including human, humanized or chimeric antibodies), polyclonal antibodies, multispecific antibodies (e.g., bispecific antibodies), Maxibody, and antibody fragments that can bind antigen (e.g., Fab', F'(ab)2, Fv, single chain antibodies, diabodies), comprising complementarity determining regions (CDRs) of the foregoing as long as they exhibit the desired biological activity.

Exemplary antibodies are Herceptin® (Trastuzumab), a recombinant DNA-derived humanized monoclonal antibody that selectively binds to the extracellular domain of the human epidermal growth factor receptor 2 (Her2) proto-oncogene; and Rituxan® (Rituximab), a genetically engineered chimeric murine/human monoclonal antibody direaed against the CD20 antigen found on the surface of normal and malignant B lymphocytes. Other exemplary antibodies include Avastin® (bevacizumab), Bexxar® (Tositumomab), Campath® (Alemtuzumab), Erbitux® (Cetuximab), Humira® (Adalimumab), Raptiva® (efalizumab), Remicade® (Infliximab), ReoPro® (Abciximab), Simulect® (Basiliximab), Synagis® (Palivizumab), Xolair® (Omalizumab), Zenapax® (Daclizumab), Zevalin®(Ibritumomab Tiuxetan), or Mylotarg® (gemtuzumab ozogamicin), receptors or soluble receptors, enzymes, variants, derivatives, or analogs of any of these antibodies.

Peptibodies, molecules comprising an antibody Fc domain attached to at least one antigen-binding peptide, are generally described in PCT publication WO 00/24782, published May 4, 2000. Immunoglobulin-like proteins, members of the immunoglobulin superfamily, contain one or more immunoglobulin-like domains which fold in structures similar to portions of the antibody variable region.

Engineering Host Cells to Overexpress Protein

Host cells can be engineered to overexpress a protein in a variety of ways known in the art, including but not limited to insertion of exogenous nucleic acid encoding the desired protein, optionally as part of an expression vector, insertion of an exogenous expression control sequence such that it causes increased expression of the host cell's endogenous gene encoding the desired protein, or activation of the host cell's endogenous expression control sequence(s) to increase expression of endogenous gene encoding the desired protein.

Cultures of host cells can be prepared according to any methods known in the art, and methods of growing such host cells and recovering recombinant protein produced by the cells, whether from the cells or culture medium, are known in the art. Such culturing methods may involve addition of chemical inducers of protein production to the culture medium. Exemplary host cells and procedures are described below.

A nucleic acid encoding a MAN1C1 polypeptide may be inserted into an appropriate expression vector using standard ligation techniques. Expression vectors optionally may include a promoter, one or more enhancer sequences, an origin of replication, a transcriptional termination sequence, a complete intron sequence containing a donor and acceptor splice site, a sequence encoding a leader or signal sequence for polypeptide secretion, a ribosome binding site, a polyadenylation sequence, a polylinker region for inserting the nucleic acid encoding the polypeptide to be expressed, and/or a selectable marker element. Each of these sequences is discussed below.

Optionally, the vector may contain a "tag"-encoding sequence, i.e., an oligonucleotide sequence located at the 5' or 3' end of the MAN1C1 polypeptide coding sequence; the oligonucleotide molecule encodes polyHis (such as hexa-His), or another "tag" such as FLAG, HA (hemaglutinin influenza virus) or myc for which commercially available antibodies exist. This tag is typically fused to the polypeptide upon expression of the polypeptide, and can serve as, a means for detection or affinity purification of the MAN1C1 polypeptide from the host cell.

Suitable vectors include, but are not limited to, cosmids, plasmids, or modified viruses, but it will be appreciated that the vector system must be compatible with the selected host cell. Nucleic acid can be transferred into host cells by any means known in the art, e.g. through liposome-mediated transfer, receptor-mediated transfer (ligand-DNA complex), electroporation, microinjection of DNA, cell fusion, DEAE-dextran, calcium chloride, calcium phosphate precipitation, microparticle bombardment, infection with viral vectors, lipofection, transfection, or homologous recombination.

The invention also contemplates use of homologous recombination or other recombinant production methods utilizing control elements introduced into cells already containing DNA encoding MAN1C1 polypeptides. For example, homologous recombination methods may be used to modify a cell that contains a normally transcriptionally silent MAN1C1 gene, or an under expressed gene, and thereby produce a cell which expresses therapeutically efficacious amounts of MAN1C1 polypeptides. Homologous recombination is a technique originally developed for targeting genes to induce or correct mutations in transcriptionally active genes (Kucherlapati, Prog. Nucl. Acid Res. & Mol. Biol. 36: 301, 1989). The basic technique was developed as a method for introducing specific mutations into specific regions of the mammalian genome (Thomas et al., Cell 44: 419-428, 1986; Thomas et al., Cell 51:503-512, 1987; Doetschman et al., Proc. Natl. Acad. Sci. 85: 8583-8587, 1988) or to correct specific mutations within defective genes (Doetschman et al., Nature 330: 576-578, 1987). Exemplary homologous recombination techniques are described in U.S. Pat. No. 5,272,071 (EP 9193051, EP Publication No. 505500; PCT/US90/07642, International Publication No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it, is possible for the new sequence of DNA to serve as the template. Thus, the transferred DNA is incorporated into the genome.

Attached to these pieces of targeting DNA are regions of DNA which may interact with or control the expression of a MAN1C1 polypeptide, e.g., flanking sequences. For example, a promoter and/or enhancer element, or an exogenous transcription modulatory element, optionally including an intron, is inserted in the genome of the intended host cell in proximity and orientation sufficient to influence the transcription of DNA encoding the desired MAN1C1 polypeptide. The control element controls a portion of the DNA present in the host cell genome. Thus, the expression of MAN1C1 polypeptide may be achieved not by transfection of DNA that encodes the MAN1C1 gene itself, but rather by the use of targeting DNA (containing regions of homology with the endogenous gene of interest) coupled with DNA regulatory segments that provide the endogenous gene sequence with recognizable signals for transcription of a MAN1C1 polypeptide.

In an exemplary embodiment, DNA which includes at least a regulatory sequence, an exon and a splice donor site is introduced into the chromosomal DNA in such a manner as to produce a new transcription unit (in which the regulatory sequence, the exon and the splice donor site present in the DNA construct are operatively linked to the endogenous gene).

Overexpression, as described herein, encompasses activating (or causing to be expressed) a gene which is normally silent (unexpressed) in the cell as obtained, as well as increasing the expression of a gene which is not expressed at physiologically significant levels in the cell as obtained.

Site-specific recombination systems such as Cre/loxP, FLP/FRT are known in the art (Sauer, Curr. Opin. Biotechnol. 521-527, 1994; Sauer, Meth. Enzymol. 225: 890-900, 1993).

An additional approach for increasing, or causing, the expression of MAN1C1 polypeptide from a cell's endogenous MAN1C1 gene involves increasing the expression of transcription factors that upregulate expression of the gene and/or decreasing the expression of transcriptional repressors that downregulate expression of the gene, in a manner which results in de novo or increased MAN polypeptide production from the cell's endogenous MAN1C1 gene.

Thus, the invention contemplates host cells into which nucleic acid encoding MAN1C1 has been inserted, optionally operably linked to an expression control sequence, and optionally as part of an expression vector. The invention also contemplates host cells into which a heterologous expression control sequence has been inserted in such a manner as to increase MAN1C1 expression, including host cells in which the native MAN1C1 gene is operably linked to a heterologous expression control sequence.

Any host cells or hosts known in the art for recombinant protein production may be used, including yeast cells, plant cells, plants, insect cells, and mammalian cells, and transgenic animals. Exemplary yeast cells include *Pichia*, e.g. *P. pastoris*, and *Saccharomyces* e.g. *S. cerevisiae*, as well as *Schizosaccharomyces pombe*, *Kluyveromyces*, *K. Zactis*, *K. fragilis*, *K. bulgaricus*, *K. wickeramii*, *K. waltii*, *K. drosophilarum*, *K. thernotolerans*, and *K. marxianus; K. yarrowia; Trichoderma reesia, Neurospora crassa, Schwanniomyces, Schwanniomyces occidentalis, Neurospora, Penicillium, Totypocladium, Aspergillus, A. nidulans, A. niger, Hansenula, Candida, Kloeckera, Torulopsis*, and *Rhodotorula*. Exemplary insect cells include *Autographa californica* and *Spodoptera frugiperda*, and *Drosophila*. Exemplary mammalian cells include varieties of CHO, BHK, HEK-293, NS0, YB2/3, SP2/0, and human cells such as PER-C6 or HT1080, as well as VERO, HeLa, COS, MDCK, NIH3T3, Jurkat, Saos, PC-12, HCT 116, L929, Ltk-, WI38, CV1, TM4, W138, Hep G2, MMT, a leukemic cell line, embryonic stem cell or fertilized egg cell.

Culturing Methods and Polypeptide Production

The invention also provides methods for culturing, i.e. growing, host cells under conditions that increase MAN1C1 protein expression and result in increased specific productivity or protein production of any of the recombinant proteins of interest described herein. Such methods may further include the step of recovering the recombinant protein of interest produced from the host cells or culture medium.

When the recombinant protein of interest is secreted into the medium, the medium can be harvested periodically, so that the same host cells can be used through several harvest cycles. In exemplary embodiments, host cells producing erythropoiesis-stimulating molecules are incubated in three discrete batch harvest cycles. For each cycle, medium is harvested and replaced with fresh medium replacing the harvested medium. The first cycle may be, e.g., 8 days; the second cycle, e.g., 7 days; and the third cycle, e.g., 5 days in duration.

A variety of culture systems are known in the art, including T-flasks, spinner and shaker flasks, roller bottles and stirred-tank bioreactors. Roller bottle cultivation is generally carried out by seeding cells into roller bottles that are partially filled (e.g., to 10-30% of capacity) with medium and slowly rotated, allowing cells to attach to the sides of the bottles and grow to confluency. The cell medium is harvested by decanting the supernatant, which is replaced with fresh medium. Anchorage-dependent cells can also be cultivated on microcarrier, e.g. polymeric spheres, that are maintained in suspension in stirred-tank bioreactors. Alternatively, cells can be grown in single-cell suspension.

Culture medium may be added in a batch process, e.g. where culture medium is added once to the cells in a single batch, or in a fed batch process in which small batches of culture medium are periodically added. Medium can be harvested at the end of culture or several times during culture. Continuously perfused production processes are also known in the art, and involve continuous feeding of fresh medium into the culture, while the same volume is continuously withdrawn from the reactor. Perfused cultures generally achieve higher cell densities than batch cultures and can be maintained for weeks or months with repeated harvests.

Host cells of the invention may be cultured using standard media well known to the skilled artisan. The media will usually contain all nutrients necessary for the growth and survival of the cells. Suitable media for culturing eukaryotic cells are, Roswell Park Memorial Institute medium 1640 (RPMI 1640), Minimal Essential Medium (MEM), and/or Dulbecco's Modified Eagle Medium (DMEM), all of which may be supplemented with serum and/or growth factors as indicated by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, geneticin, and neomycin.

The amount of a MAN1C1 polypeptide and the amount of desired recombinant protein of interest produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, and/or activity assays such as DNA binding gel shift assays. The invention also contemplates that specific productivity (expressed as pg/cell/day) of protein of interest can be evaluated using standard methods as known in the art and as described herein.

EXAMPLES

The present invention is described in more detail with reference to the following non-limiting examples, which are offered to more fully illustrate the invention, but are not to be construed as limiting the scope thereof. The examples illustrate various methods used in the invention, such as cell culture methods; recombinant HuEPO quantitation by RP-HPLC; analysis of gene expression using Affymetrix chips; quantitative real time PCR of selected genes; the use of MAN1C1 siRNA; and MAN1C1 cloning and expression. The examples also illustrate the effect of sodium butyrate on rHuEPO specific productivity and cell cycle progression; the effect of sodium butyrate on MAN1C1 expression; the effect of MAN1C1 small interfering RNA (siRNA) on rHuEPO specific productivity; and the effect of the overexpression of MAN1C1 on rHuEPO specific productivity.

The techniques described in these examples represent techniques described by the inventors to function well in the practice of the invention, and as such constitute exemplary modes for the practice thereof. Many changes can be made in the specific methods that are disclosed and still obtain a like or similar result without departing from the spirit and scope of the invention. Such variations are intended as aspects of the invention.

Example 1

Cell Culture Methods

A human kidney fibrosarcoma cell line, HT1080 (Rasheed et al., *Cancer* 33: 1027-1033, 1974), transfected with a plasmid for human EPO cDNA was used throughout the experiments described in the Examples as set out below. Selective pressure for the retention of the transfected plasmid was maintained with the antibiotic geneticin (Gibco). Cells were grown as attached monolayers in vented T-flasks (75 cm$^2$) (Corning) at an inoculation density of $2.1 \times 10^4$ cells/cm$^2$ in a humidified 12% $CO_2$ incubator at 37° C. Cells were grown for 4-5 days in 10% serum containing DMEM media supplemented with 1× Non-Essential amino acids, 5 mg/L geneticin, and 1.5 g/L sodium bicarbonate (all from Gibco). After cells reached confluence, they were washed with PBS to remove the serum and switched to serum-free 1:1 DMEM/F-12 media supplemented with 1× Non-Essential amino acids (Gibco), 1.5 g/L sodium bicarbonate, and 2 g/L glucose for a period of 5 to 7 days. Experimental cultures were treated with 2 mM sodium butyrate (Sigma) on the same day as the serum-free media addition.

Example 2

Recombinant HuEPO Quantitation by RP-HPLC

To determine the amount of recombinant human erythropoietin (rHuEPO) produced in cell culture media, 200 μl of media were analyzed by reversed phase HPLC. Samples were separated on an analytical styrene/divinylbenzene HPLC column equipped with a guard column (Polymer Labs) using a linear gradient from 30-65% $CH_3CN$ in 0.1% TFA over 17 minutes (Sigma). The retention time for rHuEPO expressed in cell culture was approximately 15.5 minutes and corresponded with a purified rHuEPO standard (Amgen Inc). Integrated peak areas of unknown samples were quantitated by comparison to a standard curve of purified rHuEPO.

Example 3

Analysis of Gene Expression Using Affymetrix Chip

The expression of genes in HT1080 cells was studied over a 24 hour period in the presence and absence of sodium butyrate using oligonucleotide microarrays and the HU133A Affymetrix chip (Affymetrix). All experiments were carried out according to Affymetrix protocols. A total of 24 chips were analyzed—12 from sodium butyrate-treated cells and 12 controls. The gene expression data from the Affymetrix software was first imported into GeneSpring® version 6.0 and normalized using the software's global normalization procedure. Values below 0.01 were set to 0.01 and each measurement wash divided by the $50^{th}$ percentile of all measurements for that sample. Each gene was then divided by the median of its measurements in all samples, and if the median of the raw values was below 10, then each measurement for that gene was divided by 10. Sample data for each chip was then grouped by treatment type (control or sodium butyrate) and by time (3, 6, 12, and 24 hours). Results from the expression data were compared to the publicly available gene list from the Consortium for functional Glycomics cDNA array (GLYCOv2 Gene Chip) for genes present in four categories: glycan degradation, glycan transferase, glycan transport, and sugar nucleotides, as defined by the Consortium gene list.

Example 4

Quantitative Real Time PCR of Selected Genes

TaqMan (Applied Biosystems Inc.) reverse transcription quantitative real time PCR (qRT-PCR) was used to verify the changes in mRNA expression seen using the Affymetrix chip. Probes to MAN1C1 and rHuEPO were generated using Primer Express software (Applied Biosystems Incorporated). MAN1C1: Forward—GGA GCC CCA GAG CCA AGT (SEQ ID NO: 6); Reverse—GCC AAG CAA ACT GCA TCA TCT (SEQ ID NO: 7); TaqMan—ECG AGC CCA GCG GGA GAA AAT CAX (E=6-FAM; X=Tamra) (SEQ ID NO: 8). rHuEPO: Forward—GTT AAT TTC TAT GCC TGG AAG AGG AT (SEQ ID NO: 9); Reverse—CCA GGC CCT GCC AGA CTT (SEQ ID NO: 10); TaqMan—EAG GTC GGG CAG CAG GCC GTX (E=6-FAM; X=Tamra) (SEQ ID NO: 11). An ABI 7000 or 7900 (Applied Biosystems Inc.) was used for each analysis with the following thermal cycling parameters; 1 cycle at 50° C. for 30 min; 1 cycle at 95° C. for 10 min; 40 cycles at 94° C. for 15 sec and 60° C. for 60 sec. RNA samples from at least three independent cell cultures were assayed in triplicate for both control and sodium butyrate-treated cells. The cycle threshold (Ct) values for all genes tested were normalized to the housekeeping gene, GAPDH (Applied Biosystems Inc., part #4310884E), to correct for error in RNA concentrations. Data was reported as either "fold change" or "percent change" in Ct levels for sodium butyrate treated samples as compared to control samples.

Example 5

MAN1C1 siRNA

HT1080 cells were grown in 75 cm² vented T-flasks for 4 days in 10% serum containing DMEM media supplemented with 1× Non-Essential amino acids, and 1.5 g/L sodium bicarbonate (all from Gibco). After cells reached confluence they were washed 1× with PBS and then treated with or without 50 µL siPORT™ Amine transfection agent plus 60 µM of small inhibitory RNA (siRNA) (Ambion) in 15 mL of 10% serum containing DMEM media for a period of 48 hours. Cultures were then washed with PBS to remove serum and switched into 15 mL serum free DMEM:F12 media with or without 504, siPORT™ Amine and 60 uM siRNA. Cultures were then grown for a period of 5 days in the presence and absence of 2 mM sodium butyrate. Samples of media were collected and rHuEPO and mRNA levels were assayed on Days 1, 3, and 5 post serum-free shift.

Example 6

MAN1C1 Cloning and Expression

A pENTR™221 entry vector containing the cDNA sequence of MAN1C1 (SEQ ID NO: 1) and flanking attL recombination sites was used (Invitrogen—clone ID:IOH42767). Following the gateway technology procedure, recombination, using LR Clonase™ of the entry clone two attL sites with the destination pcDNA3.1/nV5-DEST™ vector two attR sites, was performed and verified by transformation of DH5α competent cells under ampicillin selection. (The destination vector contains the ccdB gene that allows for negative selection in the recombination reaction.) Restriction enzyme digestion of the destination vector after recombination and transformation with BamHI confirmed the proper recombination reaction (data not shown). A plasmid preparation of DNA (~3 mg) was obtained using the manufacturer's protocol for the Giga Prep Plasmid DNA Kit (Qiagen).

Transfection of HT1080 cells was performed as follows: T-flasks (75 cm²) were inoculated at 1.6×10⁶ cells and allowed to grow for 4 to 5 days prior to transfection. Either 16, 32, or 64 µg of plasmid DNA was added to 2 mL of DMEM:F12 media. In addition, 59 µL Lipofectamine 2000 (Invitrogen) was added to a separate 2 mL of DMEM:F12 media and incubated for 5 minutes. The two mixtures of DNA and Lipofectamine were then combined and allowed to incubate for 20 minutes at room temperature. Following a 1×PBS wash of the T-flasks, the entire mixture (~4 mL) was added and allowed to incubate for 2 hours in a 37° C./12% $CO_2$ incubator. An additional 11 mL of fresh DMEM:F12 media was added to each T-flask, and sampling began 24 hours later.

Example 7

Sodium Butyrate Increases rHuEPO Specific Productivity and Blocks Cell Cycle Progression The effect that sodium butyrate treatment has on the HT1080 cell cycle and rHuEPO specific productivity was examined. Cells treated with sodium butyrate (2 mM) increased recombinant human erythropoietin (rHuEPO) specific productivity roughly four-fold compared to control cultures (FIG. 1). However, instead of sodium butyrate shifting the cells into the G0/G1 phase, where other investigators have reported protein synthesis is maximized (Kim et al., *Biotech. Bioeng.* 71: 184, 2001), the population of cells in G0/G1, S, and G2/M-phases remained relatively constant over the entire 5 days of culture as compared to control cultures. These differences may be due to the culturing methods as set out above, which allowed the cells to reach confluence prior to the addition of sodium butyrate, whereas previous reports looked at cell cycle effects on exponentially growing cells at the time of sodium butyrate addition. Therefore, cell cycle data alone cannot be responsible for the increases in rHuEPO specific productivity that were measured.

Example 8

Sodium Butyrate Increases MAN1C1 Expression

Recombinant HuEPO, produced in HT1080 cultures, was used as a model glycoprotein to study the effects of sodium butyrate on genes involved in protein glycosylation. Treatment of HT 1080 cells with 2 mM sodium butyrate in culture resulted in numerous phenotypic changes with respect to sugar nucleotide pools and the oligosaccharide structures present on rHuEPO.

To determine if these phenotypic changes were associated with genetic changes, the expression of genes in HT1080 cells was studied over a 24 hour period in the presence and absence of sodium butyrate using oligonucleotide microarrays and the HU133A Affymetrix chip (Affymetrix).

A potential rate-limiting enzyme, alpha 1,2 mannosidase I enzyme (MAN1C1), involved in glycoprotein N-linked oligosaccharide processing, was identified. The relative change in MAN1C1 mRNA induced by sodium butyrate is set forth below in Table 1. This gene increased in expression roughly 10-fold over the course of twenty-four hours when cells were treated with sodium butyrate (Table 1). Subsequent validation of the MAN expression by qRT-PCR for HT1080 cells treated with sodium butyrate over a five day period showed increases >40-fold as compared to control cultures (Table 1).

TABLE 1

Summary of qRT-PCR Data for HT1080 MAN1C1 mRNA Fold Change

| Time Point (hr)[A] | Fold Change[B] | Standard Deviation |
|---|---|---|
| 3 | 8.7 | ±2.1 |
| 6 | 38.7 | ±9.5 |
| 12 | 36.0 | ±4.6 |
| 24 | 53.3 | ±14.4 |
| 72 | 42.2 | ±3.8 |
| 120 | 7.8 | ±3.6 |

[A]Time after sodium butyrate added to culture
[B]Fold change as compared to untreated HT1080 cells Example 9

MAN1C1 Small Interfering RNA (siRNA) Reduces rHuEPO Specific Productivity

Figure 2A:
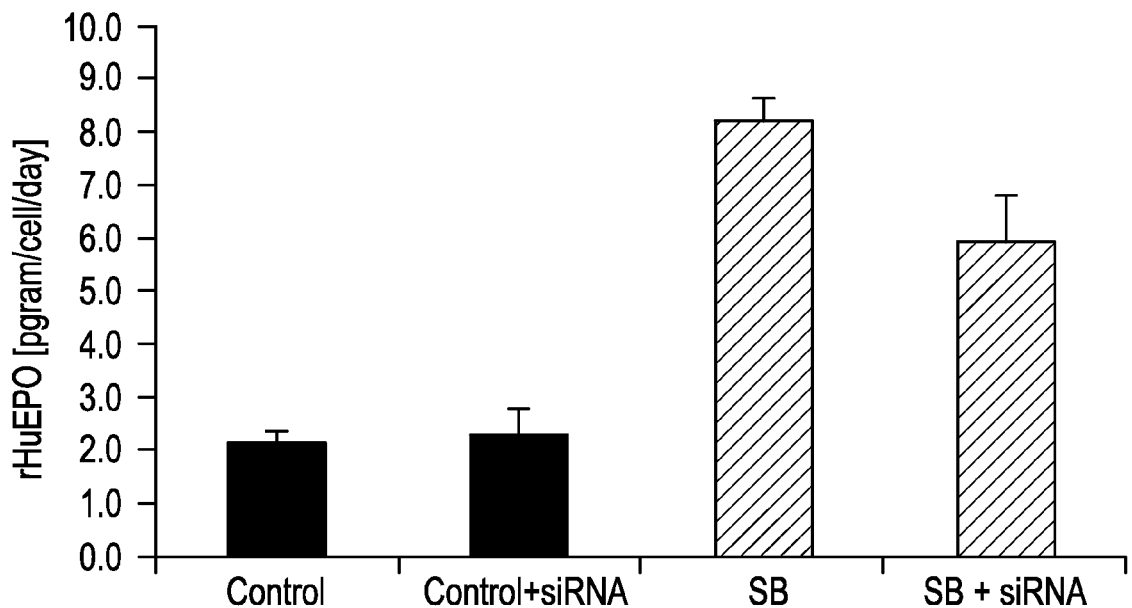
FIG. 2A shows the effect of MAN siRNA treatment on rHuEPO $Q_P$ in the presence of sodium butyrate (SB) of and absence (control) of sodium butyrate over a 5-day period.
Figure 2B:
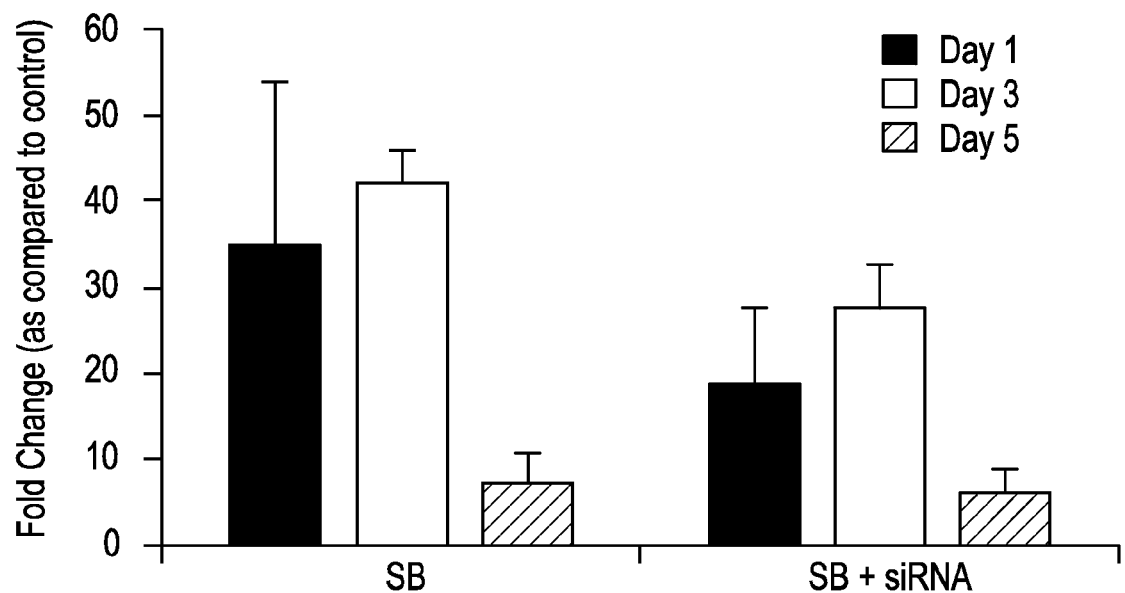
FIG. 2B displays the fold change in MAN1C1 mRNA levels in HT1080 cells treated with sodium butyrate (SB) or sodium butyrate plus siRNA (SB+siRNA) as compared to control HT1080 mRNA levels.

To determine if a link existed between sodium butyrate's effect on increases in MAN1C1 expression and increases in rHuEPO specific productivity, cells were treated with small interfering RNA (siRNA) against MAN1C1 in the presence and absence of sodium butyrate. Treatment with siRNA had no impact on rHuEPO $Q_P$ under control conditions, but decreased rHuEPO $Q_P$ 50% when cells were treated with both sodium butyrate and the siRNA as compared to sodium butyrate alone (FIG. 2A). As previously shown, sodium butyrate treatment increases MAN1C1 mRNA levels as compared to control cultures (FIG. 2B), however, cells treated with both sodium butyrate and siRNA had an ~30% decrease in MAN1C1 mRNA levels as compared to cells treated with sodium butyrate alone (FIG. 2B). It should be noted that MAN mRNA levels were still higher in the sodium butyrate and siRNA treated cells as compared to controls (FIG. 2B). This correlated to a rHuEPO $Q_p$ that remained higher than control in both cells treated with sodium butyrate alone and cells treated with sodium butyrate and siRNA, although the absolute levels of $Q_P$ were reduced (FIG. 2A).

Figure 3:
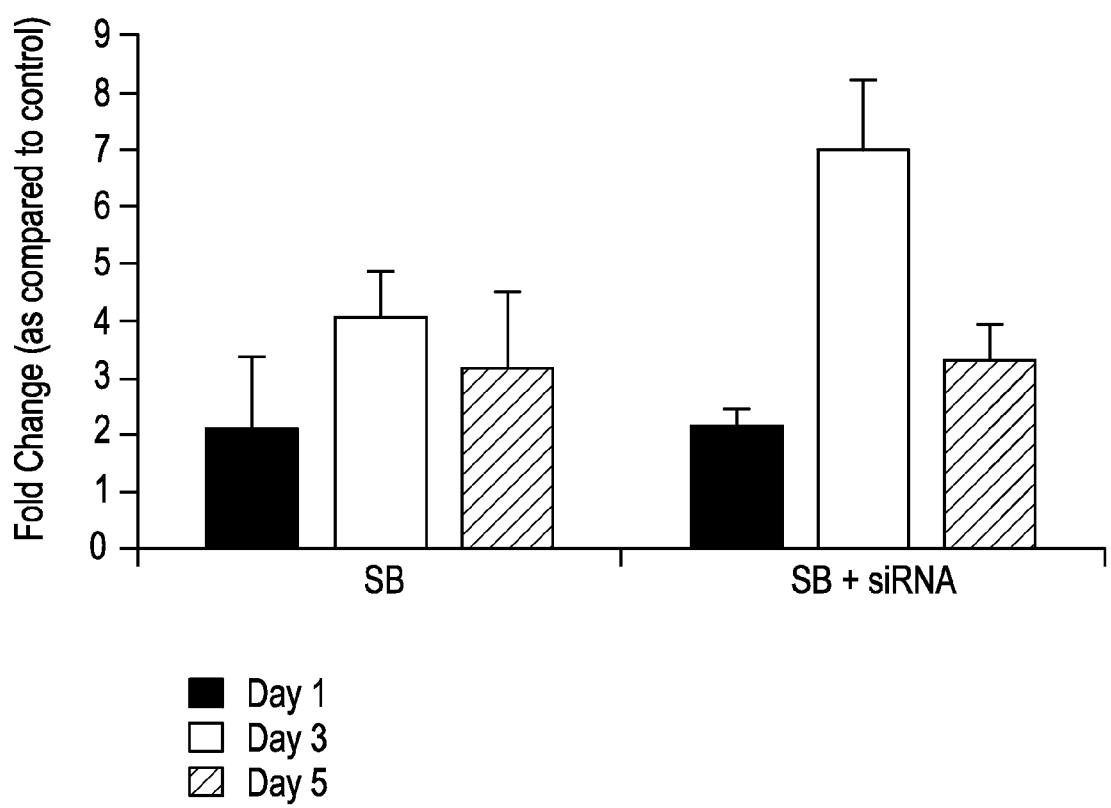
FIG. 3 displays changes in rHuEPO mRNA levels in HT1080 cells treated with sodium butyrate in the presence (SB+siRNA) and absence of siRNA (SB) directed against MAN1C1 (n=3).

To ensure that changes in specific productivity measurements were not caused by a decrease in rHuEPO mRNA levels due to off target effects of the siRNA treatment, rHuEPO mRNA levels were measured over the same five-day period. As shown in FIG. 3, rHuEPO mRNA levels were consistent on day 1 and day 5 in cells treated with sodium butyrate (+/−) siRNA, and were slightly higher on day 5 as compared to control cultures. This data confirms that the siRNA treatment for MAN1C1 did not alter rHuEPO expression levels by reducing rHuEPO mRNA abundance.

Example 10

Overexpression of MAN1C1 Increases Specific Productivity of rHuEPO

To confirm that MAN1C1 could account for the increase in rHuEPO $Q_P$, independent from sodium butyrate treatment, cells were transfected to overexpress MAN1C1 under control conditions. As seen in Table 2 (set out below), when 16-64 μg of MAN1C1 plasmid DNA was transfected into cells, a large increase (>1000 fold) in MAN1C1 mRNA levels was measured as compared to un-transfected (control) cells.

Figure 4:
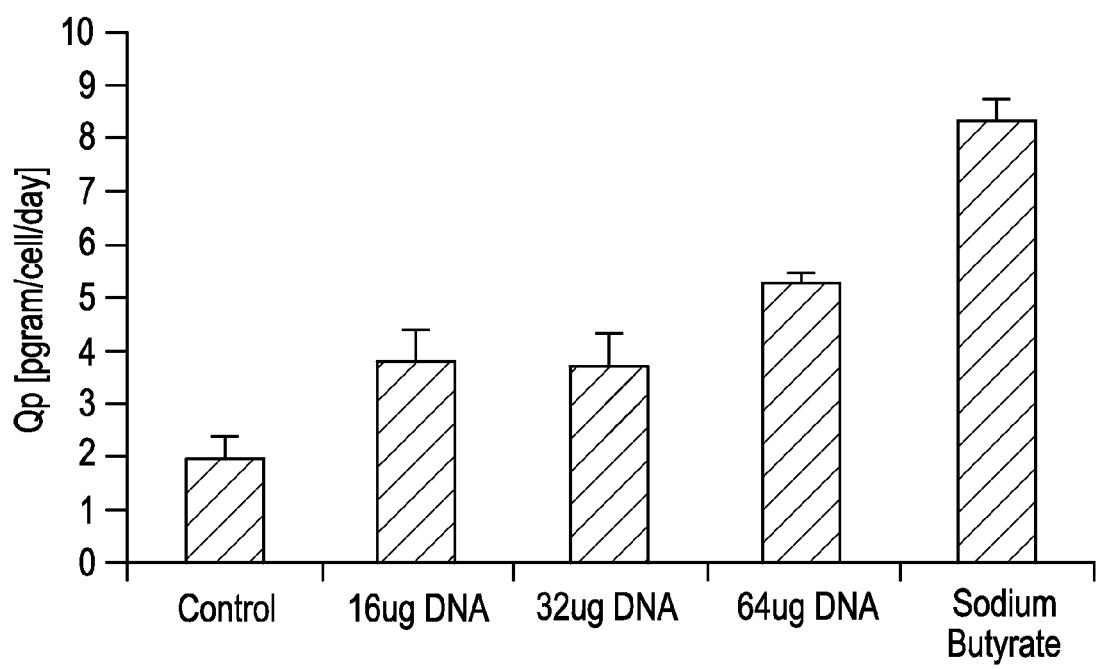
FIG. 4 displays changes in rHuEPO specific productivity after transient transfection with varying amounts of plasmid MAN1C1 DNA (n=2).

The transient expression of MAN1C1 under control conditions (e.g. no sodium butyrate addition) resulted in a 2-3 fold increase in rHuEPO specific productivity depending on the amount of plasmid DNA transfected (FIG. 4). Although the level of rHuEPO productivity is less than when sodium butyrate alone is used, the data confirms that sodium butyrate increases MAN1C1 expression, which in turn contributes to the increase in rHuEPO specific productivity.

TABLE 2

Summary of % MAN1C1 mRNA increase after transfection as compared to untransfected cells.

| | % MAN1C1 mRNA Increase (n = 2)[A] | | |
|---|---|---|---|
| Sample | Day 1 | Day 3 | Day 5 |
| 16 ug DNA | 1683% | 1817% | 2020% |
| 32 ug DNA | 1776% | 1828% | 2149% |
| 64 ug DNA | 1650% | 1774% | 2463% |

[A] % increase was calculated by the difference in the cycle at which absolute quantitation occurs (Ct—cycle threshold) between cells untransfected versus transfected.

All publications, patents and patent applications cited in this specification are herein incorporated by reference in their entirety, including but not limited to the material relevant for the reason cited, as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

I claim:

1. A method of producing a glycoprotein of interest comprising the steps of:
culturing an isolated host cell engineered to overexpress (a) alpha 1,2 mannosidase (MAN1C1) native to the host cell and (b) a glycoprotein of interest, wherein the MAN1C1 polypeptide is expressed at a level that increases specific productivity (pg/cell/day) of said glycoprotein of interest compared to an unaltered host cell in culture medium; and recovering the glycoprotein of interest from the host cell or culture medium.

2. The method of claim 1 wherein said host is cultured under conditions that induce increased MAN1C1 expression.

3. The method of claim 1 wherein said host cell expresses MAN1C1 protein at a level that increases specific productivity (pg/cell/day) of glycoprotein of interest produced.

4. The method of claim 3 wherein at least a 2-fold increase in specific productivity is achieved by overexpression of MAN1C1.

5. The method of claim 1 wherein said host cell has been transfected with a vector comprising a nucleic acid encoding MAN1C1 operably linked to a heterologous expression control sequence.

6. The method of claim 1 wherein said host cell comprises a heterologous expression control sequence operably linked to a nucleic acid encoding MAN1C1.

7. The method of claim 1 wherein said host cell has been transfected with a vector comprising a nucleic acid encoding said glycoprotein of interest operably linked to a heterologous expression control sequence.

8. The method of claim 1 wherein said host cell comprises a heterologous expression control sequence operably linked to a nucleic acid encoding said glycoprotein of interest.

9. The method of claim 1 wherein the glycoprotein of interest is an erythropoiesis-stimulating molecule.

10. The method of claim 1 wherein the glycoprotein of interest is erythropoietin of SEQ ID NO: 3.

11. The method of claim 1 wherein the glycoprotein of interest is darbepoetin of SEQ ID NO: 5.

12. The method of claim 1 wherein the host cell is a mammalian cell.

13. The method of claim 1 wherein the host cell is a CHO cell.

14. The method of claim 1 wherein the host cell is a human cell.

15. The method of claim 1 wherein the host cell is a BHK cell.

16. The method of claim 1 wherein the host cell is an NS/0 cell.

17. The method of claim 1 wherein the host cell is an HT-1080 cell.

* * * * *

SEQUENCE LISTING

<160> NUMBER OF SEQ ID NOS: 14

<210> SEQ ID NO 1
<211> LENGTH: 2912

-continued

<212> TYPE: DNA
<213> ORGANISM: Homo sapiens

<400> SEQUENCE: 1

```
aaggcgcggg cccggcgcg gcggggaggg ctcggccgga ggggaggctg cggcgcgcgg      60
ccggtcgctg cgggcccggg ccccaagccg tgccgctccg ctcgcccggg cccagccgag     120
gccgctgcgc ccccgcctcc tcgcggggagg actcgctcca aactccctga acttcgggga    180
cagtcccccg aagcggcgaa actctcaggg ttggcaaccc tgcccaggga cccccatccc    240
gggcggcgct ccggacgccc tcccctcacc gcgcccccgc agacacgtgc ctggactccg    300
agggcttctg gagccaccgg ccgggccacg atgctcatga ggaaagtgcc cggcttcgtc    360
ccggcctccc cgtgggggct gcggctgccg cagaagttcc tcttcctcct cttcctctcg    420
ggcctggtca ccctgtgctt cggggccctc ttcctgctgc cccactcctc tcgcctcaag    480
cgcctcttcc tggcccccg acccagcag cctggtctgg aagtggtggc tgaaatcgcc      540
ggccatgccc cggcccgcga gcaggagccg cctcccaacc cggcccccgc cgcgccggcc    600
ccgggcgagg atgaccccag cagctgggcc agtccccgcc gcaggaaagg ggggctgcgg    660
cgcacccgcc ccactggacc ccgcgaggag gccacggcgg cccggggcaa tagcatcccg    720
gcctccaggc ccggggacga gggcgtccct ttccgctttg acttcaacgc attccggagc    780
cgtctccgcc accggtcct gggaacgagg gccgatgaga gtcaggagcc ccagagccaa    840
gtgcgagccc agcgggagaa aatcaaggag atgatgcagt ttgcttggca gagctataag    900
cgttatgcaa tgggaaaaa cgaactccgt ccactaacaa aagatggcta cgagggtaac    960
atgttcggag gcctcagcgg ggcaacagtc attgactccc tcgatacct ctacctcatg    1020
gagctgaagg aggagttcca ggaggccaag gcctgggtgg agagagcttc ccacctgaac   1080
gtgagcggag aagcatcctt gtttgaggtg aacatccgct acatcggggg actcctctca  1140
gccttctacc tgacaggaga agaggtgttc cgaataaagg ccatcaggct gggagagaag  1200
ctcctgccgg cgttcaacac ccccacggga atcccaaagg gcgtggtgag cttcaaaagt  1260
gggaactggg gctgggccac agccggcagc agcagcatct tggcggagtt tggatccctg  1320
cacttggaat tcttacacct cactgaactc tctggcaacc aggtcttcgc tgaaaaggtc   1380
aggaacatcc gcaaggtcct caggaagatc gaaaagccct ttggcctcta ccccaacttc  1440
ctcagcccag tgagtgggaa ctgggtgcaa caccatgtct cagttggagg actcggggac  1500
agttttatg aatatttgat caaatcctgg ttgatgtcgg gcaagacaga tatggaggct   1560
aaaaatatgt actacgaagc cttggaggcg atagagacct acttgctgaa tgtctctccc  1620
gggggctga cctacattgc cgagtggcga gggggggattc tggaccacaa gatggggcac  1680
ctggcctgtt tctccggggg catgatcgcc cttggcgccg aggatgccaa ggaagaaaag   1740
agggcccact accgagagct cgcagcccag atcaccaaga cgtgtcacga gtcatacgcc   1800
cgctcagaca ccaaacttgg gcctgaggcc ttctggttta actccggcag agaggccgtg   1860
gccacccagc tgagcgagag ctactacatc ctccggccag aggtggtgga gagctacatg   1920
tacctgtggc gacagaccca caccccatc tacagggagt ggggctggga ggtggtgctg    1980
gccttggaga aatactgtcg gacagaagcc ggtttctctg gatccaagga cgtgtacagt   2040
agcacccca accacgacaa caagcagcag agcttctttc tagcggagac actaaagtat   2100
ctctatcttc tgttctctga agatgacttg ctctccctgg aagactgggt gttcaacacc   2160
gaggcccacc cactcccggt gaaccactca gacagctccg gcagagcctg gggcagacac   2220
tgaccccatc tcctgccgcc gccctggggc cgccgcaggg atgccttgcc ttttcaggat   2280
```

-continued

```
ttgagactgt tctcaaaggg attgggaacg aaggccccat ctcgggcaga cccccagcag    2340
atgtgtcgga caagcaactt cttttcctct gtgaggagac aagacttgga gactcagcga    2400
tgtcaggcca gggccatggc cacactggcc cacacattcc tttctacaga gaatttctat    2460
gaagcccact cacttgccat tccagggcca aaggaccgga ggtttgcata tccgccccttt   2520 gtatttgatt tgcttccttt tggtttcttg gttttttgttt ttgcttgatt ttgtcttttc    2580
tctacagttt agttttgtca caattacaca tatagttttc aaaatcatgc actttctaaa    2640
atggtgtcat cctgaaaaac aaaacccagt gtttgcacac acacaaaatc ttgaccccgt    2700
tatctatatt ttaaatgctt tttgcccaac actgaccta tgttcaactt tgtgtcattt     2760
accttataat ttgaggaggg gtttcccttt gggcctcagt gttacaaatt actagtgcta    2820
ttttcattat tattgtaatg gaaaaatctg tggactagaa taaagagtt tattgaataa    2880 gaaaaaaaaa aaaaaaaaa aaaaaaaaaa aa                                   2912
```

<210> SEQ ID NO 2
<211> LENGTH: 630
<212> TYPE: PRT
<213> ORGANISM: Homo sapiens

<400> SEQUENCE: 2

```
Met Leu Met Arg Lys Val Pro Gly Phe Val Pro Ala Ser Pro Trp Gly
1               5                   10                  15

Leu Arg Leu Pro Gln Lys Phe Leu Phe Leu Leu Phe Leu Ser Gly Leu
            20                  25                  30

Val Thr Leu Cys Phe Gly Ala Leu Phe Leu Leu Pro His Ser Ser Arg
        35                  40                  45

Leu Lys Arg Leu Phe Leu Ala Pro Arg Thr Gln Gln Pro Gly Leu Glu
    50                  55                  60

Val Val Ala Glu Ile Ala Gly His Ala Pro Ala Arg Glu Gln Glu Pro
65                  70                  75                  80

Pro Pro Asn Pro Ala Pro Ala Ala Pro Ala Pro Gly Glu Asp Asp Pro
                85                  90                  95

Ser Ser Trp Ala Ser Pro Arg Arg Lys Gly Gly Leu Arg Arg Thr
            100                 105                 110

Arg Pro Thr Gly Pro Arg Glu Glu Ala Thr Ala Ala Arg Gly Asn Ser
        115                 120                 125

Ile Pro Ala Ser Arg Pro Gly Asp Glu Gly Val Pro Phe Arg Phe Asp
    130                 135                 140

Phe Asn Ala Phe Arg Ser Arg Leu Arg His Pro Val Leu Gly Thr Arg
145                 150                 155                 160

Ala Asp Glu Ser Gln Glu Pro Gln Ser Gln Val Arg Ala Gln Arg Glu
                165                 170                 175

Lys Ile Lys Glu Met Met Gln Phe Ala Trp Gln Ser Tyr Lys Arg Tyr
            180                 185                 190

Ala Met Gly Lys Asn Glu Leu Arg Pro Leu Thr Lys Asp Gly Tyr Glu
        195                 200                 205

Gly Asn Met Phe Gly Gly Leu Ser Gly Ala Thr Val Ile Asp Ser Leu
    210                 215                 220

Asp Thr Leu Tyr Leu Met Glu Leu Lys Glu Phe Gln Glu Ala Lys
225                 230                 235                 240

Ala Trp Val Gly Glu Ser Phe His Leu Asn Val Ser Gly Glu Ala Ser
                245                 250                 255

Leu Phe Glu Val Asn Ile Arg Tyr Ile Gly Gly Leu Leu Ser Ala Phe
```

```
                    260                 265                 270
Tyr Leu Thr Gly Glu Glu Val Phe Arg Ile Lys Ala Ile Arg Leu Gly
                275                 280                 285
Glu Lys Leu Leu Pro Ala Phe Asn Thr Pro Thr Gly Ile Pro Lys Gly
            290                 295                 300
Val Val Ser Phe Lys Ser Gly Asn Trp Gly Trp Ala Thr Ala Gly Ser
305                 310                 315                 320
Ser Ser Ile Leu Ala Glu Phe Gly Ser Leu His Leu Glu Phe Leu His
                325                 330                 335
Leu Thr Glu Leu Ser Gly Asn Gln Val Phe Ala Glu Lys Val Arg Asn
            340                 345                 350
Ile Arg Lys Val Leu Arg Lys Ile Glu Lys Pro Phe Gly Leu Tyr Pro
                355                 360                 365
Asn Phe Leu Ser Pro Val Ser Gly Asn Trp Val Gln His His Val Ser
            370                 375                 380
Val Gly Gly Leu Gly Asp Ser Phe Tyr Glu Tyr Leu Ile Lys Ser Trp
385                 390                 395                 400
Leu Met Ser Gly Lys Thr Asp Met Glu Ala Lys Asn Met Tyr Tyr Glu
                405                 410                 415
Ala Leu Glu Ala Ile Glu Thr Tyr Leu Leu Asn Val Ser Pro Gly Gly
            420                 425                 430
Leu Thr Tyr Ile Ala Glu Trp Arg Gly Ile Leu Asp His Lys Met
                435                 440                 445
Gly His Leu Ala Cys Phe Ser Gly Met Ile Ala Leu Gly Ala Glu
            450                 455                 460
Asp Ala Lys Glu Glu Lys Arg Ala His Tyr Arg Glu Leu Ala Ala Gln
465                 470                 475                 480
Ile Thr Lys Thr Cys His Glu Ser Tyr Ala Arg Ser Asp Thr Lys Leu
                485                 490                 495
Gly Pro Glu Ala Phe Trp Phe Asn Ser Gly Arg Glu Ala Val Ala Thr
            500                 505                 510
Gln Leu Ser Glu Ser Tyr Tyr Ile Leu Arg Pro Glu Val Val Glu Ser
            515                 520                 525
Tyr Met Tyr Leu Trp Arg Gln Thr His Asn Pro Ile Tyr Arg Glu Trp
            530                 535                 540
Gly Trp Glu Val Val Leu Ala Leu Glu Lys Tyr Cys Arg Thr Glu Ala
545                 550                 555                 560
Gly Phe Ser Gly Ile Gln Asp Val Tyr Ser Ser Thr Pro Asn His Asp
                565                 570                 575
Asn Lys Gln Gln Ser Phe Phe Leu Ala Glu Thr Leu Lys Tyr Leu Tyr
            580                 585                 590
Leu Leu Phe Ser Glu Asp Asp Leu Leu Ser Leu Glu Asp Trp Val Phe
            595                 600                 605
Asn Thr Glu Ala His Pro Leu Pro Val Asn His Ser Asp Ser Ser Gly
            610                 615                 620
Arg Ala Trp Gly Arg His
625                 630

<210> SEQ ID NO 3
<211> LENGTH: 193
<212> TYPE: PRT
<213> ORGANISM: Homo sapiens
<220> FEATURE:
<221> NAME/KEY: mat_peptide
<222> LOCATION: (28)..(192)
```

<400> SEQUENCE: 3

```
Met Gly Val His Glu Cys Pro Ala Trp Leu Trp Leu Leu Leu Ser Leu
    -25                 -20                 -15
Leu Ser Leu Pro Leu Gly Leu Pro Val Leu Gly Ala Pro Pro Arg Leu
    -10                  -5              -1   1                 5
Ile Cys Asp Ser Arg Val Leu Glu Arg Tyr Leu Leu Glu Ala Lys Glu
                 10                  15                  20
Ala Glu Asn Ile Thr Thr Gly Cys Ala Glu His Cys Ser Leu Asn Glu
             25                  30                  35
Asn Ile Thr Val Pro Asp Thr Lys Val Asn Phe Tyr Ala Trp Lys Arg
         40                  45                  50
Met Glu Val Gly Gln Gln Ala Val Glu Val Trp Gln Gly Leu Ala Leu
     55                  60                  65
Leu Ser Glu Ala Val Leu Arg Gly Gln Ala Leu Leu Val Asn Ser Ser
 70                  75                  80                  85
Gln Pro Trp Glu Pro Leu Gln Leu His Val Asp Lys Ala Val Ser Gly
                 90                  95                 100
Leu Arg Ser Leu Thr Thr Leu Leu Arg Ala Leu Gly Ala Gln Lys Glu
             105                 110                 115
Ala Ile Ser Pro Pro Asp Ala Ala Ser Ala Ala Pro Leu Arg Thr Ile
         120                 125                 130
Thr Ala Asp Thr Phe Arg Lys Leu Phe Arg Val Tyr Ser Asn Phe Leu
     135                 140                 145
Arg Gly Lys Leu Lys Leu Tyr Thr Gly Glu Ala Cys Arg Thr Gly Asp
150                 155                 160                 165
Arg
```

<210> SEQ ID NO 4
<211> LENGTH: 1725
<212> TYPE: DNA
<213> ORGANISM: Homo sapiens

<400> SEQUENCE: 4

| | |
|---|---|
| gaattccctg tggaatgtgt gtcagttagg gtgtggaaag tccccaggct ccccagcagg | 60 |
| cagaagtatg caaagcatgc atctcaatta gtcagcaacc aggtgtggaa agtccccagg | 120 |
| ctccccagca ggcagaagta tgcaaagcat gcatctcaat tagtcagcaa ccatagtccc | 180 |
| gcccctaact ccgcccatcc cgcccctaac tccgcccagt tccgcccatt ctccgcccca | 240 |
| tggctgacta attttttta tttatgcaga ggccgaggcc gcctcggcct ctgagctatt | 300 |
| ccagaagtag tgaggaggct ttttggagg cctaggcttt tgcaaaaagc tggtcgagga | 360 |
| actgaaaaac cagaaagtta actggtaagt ttagtcttt tgtctttat ttcaggtccc | 420 |
| ggatccggtg gtggtgcaaa tcaaagaact gctcctcagt ggatgttgcc tttacttcta | 480 |
| ggcctgtacg gaagtgttac ttctgctcta aaagctgctg caacaagctg gtcgagatcc | 540 |
| taggtcaccc ggcgcgcccc aggtcgctga gggaccccgg ccaggcgcgg agatggggt | 600 |
| gcacgaatgt cctgcctggc tgtggcttct cctgtccctg ctgtcgctcc ctctgggcct | 660 |
| cccagtcctg ggcgccccac cacgcctcat ctgtgacagc cgagtcctgg agaggtacct | 720 |
| cttggaggcc aaggaggccg agaatatcac gacgggctgt aatgaaacgt gcagcttgaa | 780 |
| tgagaatatc actgtcccag acaccaaagt taatttctat gcctggaaga ggatggaggt | 840 |
| cgggcagcag gccgtagaag tctggcaggg cctggccctg ctgtcggaag ctgtcctgcg | 900 |
| gggccaggcc ctgttggtca actcttccca ggtgaatgag accctgcagc tgcatgtgga | 960 |

```
taaagccgtc agtggccttc gcagcctcac cactctgctt cgggctctgg gagcccagaa    1020
ggaagccatc tcccctccag atgcggcctc agctgctcca ctccgaacaa tcactgctga    1080
cactttccgc aaactcttcc gagtctactc caatttcctc cggggaaagc tgaagctgta    1140
cacaggggag gcctgcagga caggggacag atgaccaggt gtgtccacct gggcatatcc    1200
accacctccc tcaccaacat tgcttgtgcc acaccctccc ccgccactcc tgaaccccgt    1260 cgagggctc tcagctcagc gccagcctgt cccatggaca ctccagtgcc agcaatgaca    1320
tctcaggggc cagaggaact gtccagagag caactctgag atctcgacca tgggaaatgt    1380
cagagtggag aaccacaccg agtgccactg cagcacttgt tattatcaca aatcctaata    1440
gtttgcagtg ggccttgctg atgatggctg acttgctcaa aaggaaaatt aatttgtcca    1500
gtgtctatgg ctttgtgaga taaaaccctc cttttccttg ccataccatt tttaacctgc    1560
tttgagaata tactgcagct ttattgcttt tctccttatc ctacaatata atcagtagtc    1620
ttgatctttt catttggaat gaaatatggc atttagcatg accataaaaa gctgattcca    1680
ctggaaataa agtcttttaa atcatcactc tatcactgaa ttcta                    1725
```

<210> SEQ ID NO 5
<211> LENGTH: 193
<212> TYPE: PRT
<213> ORGANISM: Homo sapiens
<220> FEATURE:
<221> NAME/KEY: mat_peptide
<222> LOCATION: (28)..(192)

<400> SEQUENCE: 5

```
Met Gly Val His Glu Cys Pro Ala Trp Leu Trp Leu Leu Ser Leu
         -25             -20              -15

Leu Ser Leu Pro Leu Gly Leu Pro Val Leu Gly Ala Pro Pro Arg Leu
    -10              -5              -1   1               5

Ile Cys Asp Ser Arg Val Leu Glu Arg Tyr Leu Leu Glu Ala Lys Glu
                 10                  15                  20

Ala Glu Asn Ile Thr Thr Gly Cys Asn Glu Thr Cys Ser Leu Asn Glu
             25                  30                  35

Asn Ile Thr Val Pro Asp Thr Lys Val Asn Phe Tyr Ala Trp Lys Arg
         40                  45                  50

Met Glu Val Gly Gln Gln Ala Val Glu Val Trp Gln Gly Leu Ala Leu
     55                  60                  65

Leu Ser Glu Ala Val Leu Arg Gly Gln Ala Leu Leu Val Asn Ser Ser
 70                  75                  80                  85

Gln Val Asn Glu Thr Leu Gln Leu His Val Asp Lys Ala Val Ser Gly
                 90                  95                 100

Leu Arg Ser Leu Thr Thr Leu Leu Arg Ala Leu Gly Ala Gln Lys Glu
            105                 110                 115

Ala Ile Ser Pro Pro Asp Ala Ala Ser Ala Ala Pro Leu Arg Thr Ile
        120                 125                 130

Thr Ala Asp Thr Phe Arg Lys Leu Phe Arg Val Tyr Ser Asn Phe Leu
    135                 140                 145

Arg Gly Lys Leu Lys Leu Tyr Thr Gly Glu Ala Cys Arg Thr Gly Asp
150                 155                 160                 165

Arg
```

<210> SEQ ID NO 6
<211> LENGTH: 18
<212> TYPE: DNA
<213> ORGANISM: Artificial sequence

```
<220> FEATURE:
<223> OTHER INFORMATION: Synthetic primer

<400> SEQUENCE: 6
ggagccccag agccaagt                                                   18

<210> SEQ ID NO 7
<211> LENGTH: 21
<212> TYPE: DNA
<213> ORGANISM: Artificial sequence
<220> FEATURE:
<223> OTHER INFORMATION: Synthetic primer

<400> SEQUENCE: 7
tctactacgt caaacgaacc g                                               21

<210> SEQ ID NO 8
<211> LENGTH: 22
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: The nucleotide at position 1 is attached to
      6-Fam.
<220> FEATURE:
<221> NAME/KEY: misc_feature
<222> LOCATION: (22)..(22)
<223> OTHER INFORMATION: The nucleotide at position 22 is attached to
      Tamra.

<400> SEQUENCE: 8
cgagcccagc gggagaaaat ca                                              22

<210> SEQ ID NO 9
<211> LENGTH: 26
<212> TYPE: DNA
<213> ORGANISM: Artificial sequence
<220> FEATURE:
<223> OTHER INFORMATION: Synthetic primer

<400> SEQUENCE: 9
gttaatttct atgcctggaa gaggat                                          26

<210> SEQ ID NO 10
<211> LENGTH: 18
<212> TYPE: DNA
<213> ORGANISM: Artificial sequence
<220> FEATURE:
<223> OTHER INFORMATION: Synthetic primer

<400> SEQUENCE: 10
ttcagaccgt cccggacc                                                   18

<210> SEQ ID NO 11
<211> LENGTH: 19
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: The nucleotide at position 1 is attached to
      6-Fam.
<220> FEATURE:
<221> NAME/KEY: misc_feature
<222> LOCATION: (19)..(19)
```

<223> OTHER INFORMATION: The nucleotide at position 19 is attached to Tamra.

<400> SEQUENCE: 11
aggtcgggca gcaggccgt                                                19

<210> SEQ ID NO 12
<211> LENGTH: 3815
<212> TYPE: DNA
<213> ORGANISM: Homo sapiens

<400> SEQUENCE: 12

| | | | | | |
|---|---|---|---|---|---|
| ggctgcggcg | cacccgcccc | actggacccc | gcgaggaggc | cacggcggcc | cggggcaata | 60 |
| gcatcccggc | ctccaggccc | ggggacgagg | gcgtcccttt | ccgctttgac | ttcaacgcat | 120 |
| tccggagccg | tctccgccac | ccggtcctgg | aacgagggc | cgatgagagt | caggagcccc | 180 |
| agagccaagt | gcgagcccag | cgggagaaaa | tcaaggagat | gatgcagttt | gcttggcaga | 240 |
| gctataagcg | ttatgcaatg | gggaaaaacg | aactccgtcc | actaacaaaa | gatggctacg | 300 |
| agggtaacat | gttcggaggc | ctcagcgggg | caacagtcat | tgactccctc | gatccctct | 360 |
| acctcatgga | gctgaaggag | gagttccagg | aggccaaggc | ctgggtggga | gagagcttcc | 420 |
| acctgaacgt | gagcggagaa | gcatccttgt | ttgaggtgaa | catccgctac | atcggggac | 480 |
| tcctctcagc | cttctacctg | acaggagaag | aggtgttccg | aataaaggcc | atcaggctgg | 540 |
| gagagaagct | cctgccggcg | ttcaacaccc | cacgggaat | cccaaagggc | gtggtgagct | 600 |
| tcaaagtgg | gaactgggc | tgggccacag | ccggcagcag | cagcatcttg | gcggagtttg | 660 |
| gatccctgca | cttggaattc | ttacacctca | ctgaactctc | tggcaaccag | gtcttcgctg | 720 |
| aaaaggtcag | gaacatccgc | aaggtcctca | ggaagatcga | aaagcccttt | ggcctctacc | 780 |
| ccaacttcct | cagcccagtg | agtgggaact | gggtgcaaca | ccatgtctca | gttggaggac | 840 |
| tcggggacag | tttttatgaa | tatttgatca | aatcctggtt | gatgtcggc | aagacagata | 900 |
| tggaggctaa | aaatatgtac | tacgaagcct | tggaggcgat | agagacctac | ttgctgaatg | 960 |
| tctctcccgg | ggggctgacc | tacattgccg | agtggcgagg | ggggattctg | gaccacaaga | 1020 |
| tggggcacct | ggcctgtttc | tccgggggca | tgatcgccct | tggcgccgag | gatgccaagg | 1080 |
| aagaaaagag | ggcccactac | cgagagctcg | cagcccagat | caccaagacg | tgtcacgagt | 1140 |
| catacgcccg | ctcagacacc | aaacttgggc | ctgaggcctt | ctggtttaac | tccggcagag | 1200 |
| aggccgtggc | cacccagctg | agcgagagct | actacatcct | ccggccagag | gtggtggaga | 1260 |
| gctacatgta | cctgtggcga | cagacccaca | accccatcta | cagggagtgg | ggctgggagg | 1320 |
| tggtgctggc | cttggagaaa | tactgtcgga | cagaagccgg | tttctctggg | atccaagacg | 1380 |
| tgtacagtag | cacccccaac | cacgacaaca | agcagcagag | cttctttcta | gcggagacac | 1440 |
| taaagatttg | agactgttct | caaagggatt | gggaacgaag | gcccatctc | gggcagaccc | 1500 |
| ccagcagatg | tgtcggacaa | gcaacttctt | ttcctctgtg | aggagacaag | acttggagac | 1560 |
| tcagcgatgt | caggccaggg | ccatggccac | actggcccac | acattccttt | ctacagagaa | 1620 |
| tttctatgaa | gcccactcac | ttgccattcc | agggccaaag | gaccggaggt | ttgcatatcc | 1680 |
| gccccttgta | tttgatttgc | ttccttttgg | tttcttggtt | tttgttttg | cttgatttg | 1740 |
| tcttttctct | acagtttagt | tttgtcacaa | ttacacatat | agttttcaaa | atcatgcact | 1800 |
| ttctaaaatg | gtgtcatcct | gaaaacaaa | acccagtgtt | tgcacacaca | caaaatcttg | 1860 |
| acccccgttat | ctatattta | aatgcttttt | gcccaacact | gacccctatgt | tcaactttgt | 1920 |
| gtcatttacc | ttataatttg | aggagggtt | tccctttggg | cctcagtgtt | acaaattact | 1980 |

```
agtgctattt tcattattat tgtaatggaa aaatctgtgg actagaataa aagagtttat    2040
tgaataagaa atatgattgg gctcattgca catcagtgac tcctagaaaa accattgcaa    2100
tgttaccatc agaaataata atcagccagc agttgattta aggtataatt tagtaaacga    2160
ttccaacttc tattacctcc cctgaaatcg gtcctgatat attcgagaag catgaggcca    2220
gcccttcaga tgcagttgtt tatttatact caggtttaga ttgggaagag gcccagggag    2280
gagcagcaac ttgcctgagg tcacacagcc caaaaaaggc aaaggagagt ctcgcccctg    2340
ccgtctcctg gccaccccag ttgagtgtcc gtctgttcca tcattcagca gatgcttggt    2400
gagtgcctgc aacggaccag acactgggct agaggccagg acaccgctg agagtgagac    2460 agtcataagc cctgcagtca aggggtcaag aggggagaaa gcgatggtaa gggaaactga    2520
caagtaagtg aagtgactgc aggtcatagg aaatgctaca aaggagatag atagacagct    2580
gaggacctac cctacggggt cagggagggc ctctctgggc aggtgaccct caagccaaga    2640
cccagaagat aaaaaggagc agccgaaaga ctatctggca gaagaatgaa cttcccataa    2700
cccagccccc tttcccaccc tccctgatgc cctccctggg aggggcctg aaacactggg    2760 gctgttgtgc agagcaagga gctcaggtcc taacactgaa gtgacagctc ttcctcccct    2820 gaccctttt ttttttttga gacccagagt ctcattcagt cgcccaggct ggagtgcagt    2880
ggtgcaatct ggctcactg caacctccac ctcctgggtt caagcagttc tcctgcctca    2940
gcttccccag tagcagggtg cgtcaccaca cccggctaat ttttttgtatt tttagtaaag    3000 acgaggtttt gccatgttgc ctaggctggt cttgaactcc tgagctcagg tgatccgccc    3060
acctcagcct cccaaagtgc ggggattaca ggcatgagcc accacaccca gtcctttcct    3120
ggcacatttg cagcttgtca acacagcgga aatcacggga gaatgttgag cccttccctg    3180
ggctcagctg cttgctctgt tcataagctt taatagcccc cggggctctg gccaggtga     3240 cccggcttta aatccctgct gtgtgaactt aggcaggtac ctcccctctc tgggctcttc    3300
ttttccatca agcagacaga aaacctcaac cccacaaggt tgctgtgaga agaagtggga    3360
agctgctggt tccctgggca caggaagtgc ttgttccttg ttctggagac tcaagacatt    3420
cccagaatct tcttaagcag agctgctggg gagtagcccc tgtagcaagt accatgctct    3480
tgacaggcag catgagagcg tgactcccat gacccacctg tgctcaaaaa aaaaaaaaaa    3540
aaaaaaaaaa aagcaaacca ggaaaactga ctacacaaac attgtagaaa gattagaaaa    3600
tagaagcaga aagaagactc attggccatc ccactctctg gggtgaatac tgttatattt    3660
tcttctaggc cttttctat gaatatatag aatatagatt ttgccaccgt ggtatcctac     3720
tatgcacact gttttcttat aatctgcttt tgcacttaac tgtacattgt gaacctcttt    3780
ccatgtcaac aaatacatgt ttatctcatc gctgt                              3815
```

<210> SEQ ID NO 13
<211> LENGTH: 482
<212> TYPE: PRT
<213> ORGANISM: Homo sapiens

<400> SEQUENCE: 13

```
Leu Arg Arg Thr Arg Pro Thr Gly Pro Arg Glu Glu Ala Thr Ala Ala
1               5                   10                  15

Arg Gly Asn Ser Ile Pro Ala Ser Arg Pro Gly Asp Glu Gly Val Pro
            20                  25                  30

Phe Arg Phe Asp Phe Asn Ala Phe Arg Ser Arg Leu Arg His Pro Val
        35                  40                  45
```

```
Leu Gly Thr Arg Ala Asp Glu Ser Gln Glu Pro Gln Ser Gln Val Arg
    50                  55                  60
Ala Gln Arg Glu Lys Ile Lys Glu Met Met Gln Phe Ala Trp Gln Ser
65                  70                  75                  80
Tyr Lys Arg Tyr Ala Met Gly Lys Asn Glu Leu Arg Pro Leu Thr Lys
                85                  90                  95
Asp Gly Tyr Glu Gly Asn Met Phe Gly Gly Leu Ser Gly Ala Thr Val
            100                 105                 110
Ile Asp Ser Leu Asp Thr Leu Tyr Leu Met Glu Leu Lys Glu Glu Phe
        115                 120                 125
Gln Glu Ala Lys Ala Trp Val Gly Glu Ser Phe His Leu Asn Val Ser
    130                 135                 140
Gly Glu Ala Ser Leu Phe Glu Val Asn Ile Arg Tyr Ile Gly Gly Leu
145                 150                 155                 160
Leu Ser Ala Phe Tyr Leu Thr Gly Glu Glu Val Phe Arg Ile Lys Ala
                165                 170                 175
Ile Arg Leu Gly Glu Lys Leu Leu Pro Ala Phe Asn Thr Pro Thr Gly
            180                 185                 190
Ile Pro Lys Gly Val Val Ser Phe Lys Ser Gly Asn Trp Gly Trp Ala
        195                 200                 205
Thr Ala Gly Ser Ser Ser Ile Leu Ala Glu Phe Gly Ser Leu His Leu
    210                 215                 220
Glu Phe Leu His Leu Thr Glu Leu Ser Gly Asn Gln Val Phe Ala Glu
225                 230                 235                 240
Lys Val Arg Asn Ile Arg Lys Val Leu Arg Lys Ile Glu Lys Pro Phe
                245                 250                 255
Gly Leu Tyr Pro Asn Phe Leu Ser Pro Val Ser Gly Asn Trp Val Gln
            260                 265                 270
His His Val Ser Val Gly Gly Leu Gly Asp Ser Phe Tyr Glu Tyr Leu
        275                 280                 285
Ile Lys Ser Trp Leu Met Ser Gly Lys Thr Asp Met Glu Ala Lys Asn
    290                 295                 300
Met Tyr Tyr Glu Ala Leu Glu Ala Ile Glu Thr Tyr Leu Leu Asn Val
305                 310                 315                 320
Ser Pro Gly Gly Leu Thr Tyr Ile Ala Glu Trp Arg Gly Gly Ile Leu
                325                 330                 335
Asp His Lys Met Gly His Leu Ala Cys Phe Ser Gly Gly Met Ile Ala
            340                 345                 350
Leu Gly Ala Glu Asp Ala Lys Glu Lys Arg Ala His Tyr Arg Glu
                355                 360                 365
Leu Ala Ala Gln Ile Thr Lys Thr Cys His Glu Ser Tyr Ala Arg Ser
    370                 375                 380
Asp Thr Lys Leu Gly Pro Glu Ala Phe Trp Phe Asn Ser Gly Arg Glu
385                 390                 395                 400
Ala Val Ala Thr Gln Leu Ser Glu Ser Tyr Tyr Ile Leu Arg Pro Glu
                405                 410                 415
Val Val Glu Ser Tyr Met Tyr Leu Trp Arg Gln Thr His Asn Pro Ile
            420                 425                 430
Tyr Arg Glu Trp Gly Trp Glu Val Val Leu Ala Leu Glu Lys Tyr Cys
        435                 440                 445
Arg Thr Glu Ala Gly Phe Ser Gly Ile Gln Asp Val Tyr Ser Ser Thr
    450                 455                 460
Pro Asn His Asp Asn Lys Gln Gln Ser Phe Phe Leu Ala Glu Thr Leu
465                 470                 475                 480
```

Lys Ile

<210> SEQ ID NO 14
<211> LENGTH: 735
<212> TYPE: DNA
<213> ORGANISM: Platichtys flesus

<400> SEQUENCE: 14

```
ttctatgttt ggagtcagcg gatcggctgc ccgccacaga gaggactctg tcacagccct      60
gagctgagga accctgcatt gcatcgtctc caagaaaaag tttcaatgg ttttccgaaa      120
gttgcccggt gtgtcggcct cgggcatggg tcttcgcctg tcccagaagt tcgtctttct     180
gctctttctc tcgggtctgg tcacactctg cttcggggcc ctcttctttc tgcctgactc     240
ggtccggcta aaacgcatct tcctgtccaa gacagagacg cagccggtca ccgtcggctc     300
cgggtccgag aacgatgtcc gggagcacat gaagagagcc ggcaaggagc cggagccccc     360
gcggggggtg acctccgcca aggggagac cagcaccaag ctgaagagcc tcatccgcaa     420
ggcgtccgtc tctcacgagg ccacggagga gcggccggcc ggggacagag cgcaggagga     480
cctgactctg tcccggtcca ggacggagtc cgcctcggag agagtgacct cctccgaccg     540
cgctgccggc tcggatactt tcagttacca gaagttcacg aggtgtctgc tcaaaccccc     600
gctggggagg gacggtggca agccgagcga ccccaagagc gaggagcgcc ggctgaaagt     660
caaagagatg atgaagtttg cctgggacaa ctacaagctc tacgcctggg gcaagaatga     720
gctgcggcct ctgac                                                     735
```